(12) United States Patent
Bier et al.

(10) Patent No.: US 7,692,059 B2
(45) Date of Patent: Apr. 6, 2010

(54) METHOD FOR GENERATING OVEREXPRESSION OF ALLELES IN GENES OF UNKNOWN FUNCTION

(75) Inventors: Ethan Bier, San Diego, CA (US); Annabel Guichard, La Jolla, CA (US); Shaila Srinivasan, Elmhurst, IL (US)

(73) Assignee: The Regents of the University of California, Oakland, CA (US)

( * ) Notice: Subject to any disclaimer, the term of this patent is extended or adjusted under 35 U.S.C. 154(b) by 205 days.

(21) Appl. No.: 11/726,100

(22) Filed: Mar. 20, 2007

(65) Prior Publication Data

US 2007/0186291 A1  Aug. 9, 2007

Related U.S. Application Data

(62) Division of application No. 10/263,367, filed on Oct. 1, 2002, now Pat. No. 7,193,126.

(60) Provisional application No. 60/326,546, filed on Oct. 1, 2001.

(51) Int. Cl.
*C12P 21/00* (2006.01)
*A01K 67/033* (2006.01)

(52) U.S. Cl. .................... 800/4; 800/3; 800/13

(58) Field of Classification Search .............. 800/3, 800/13, 21, 22, 25
See application file for complete search history.

(56) References Cited

OTHER PUBLICATIONS

Aigaki et al. J Neurogenetics 2001;1s:169-78.*
Duffy J.B., "GAL4 System in *Drosophila*: A Fly Geneticist's Swiss Army Knife", *Genesis*, 34:1-15 (2002).
Noll et al., "New Functions of the *Drosophila Rhomboid* Gene During Embryonic and Adult Development are Revealed by a Novel Genetic Method, Enhancer Piracy", *Development*, 120:2329-2338 (1994).
Reiter et al., "A Systematic Analysis of Human Disease-Associated Gene Sequences In *Drosophila Melanogaster*", *Genome Research*, 11:1114-1125 (2001).
Yu et al., "The *Drosophila Decapentaplegic* and *Short Gastrulation* Genes Function Antagonistically During Adult Wing Vein Development", *Development*, 122:4033-4044 (1996).

* cited by examiner

*Primary Examiner*—Q. Janice Li
(74) *Attorney, Agent, or Firm*—DLA Piper LLP (US)

(57) ABSTRACT

Methods for generating and using novel overexpression activity alleles of a gene in any organism, especially *Drosophilia*, are provided. Such alleles may be utilized in screening assays, and used to generate dominant-negative forms of bacterial toxins.

8 Claims, 15 Drawing Sheets

A
B
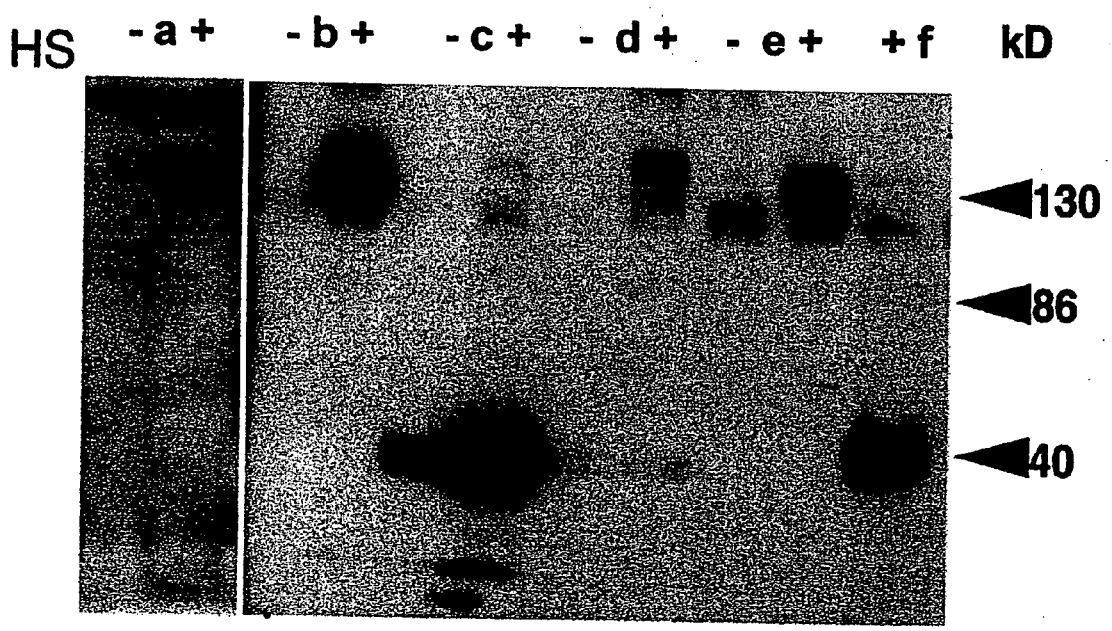
FIG. 3

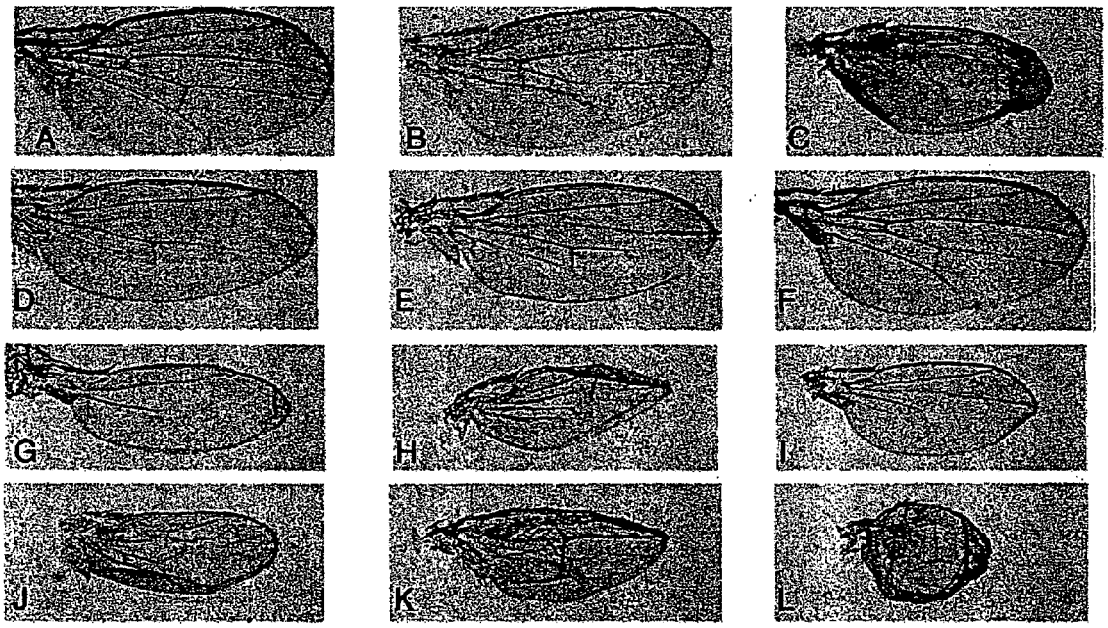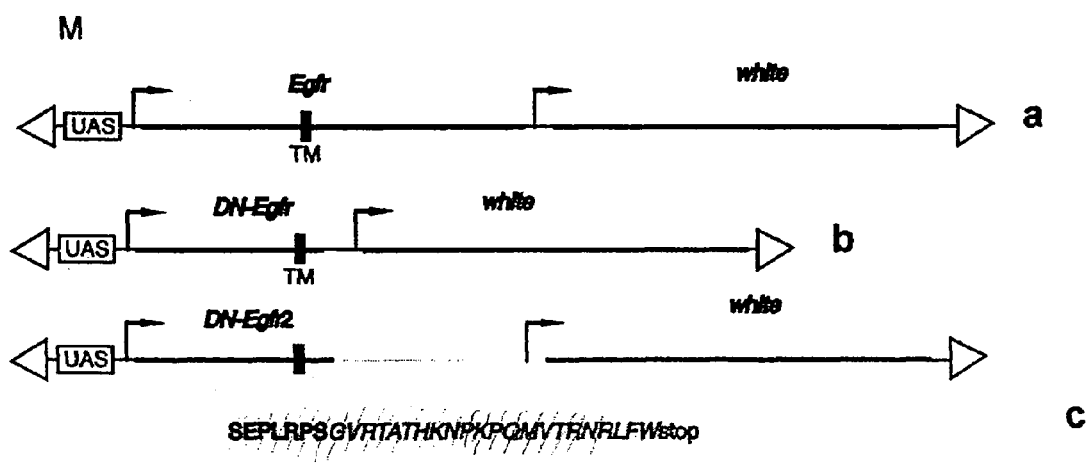
FIG. 4

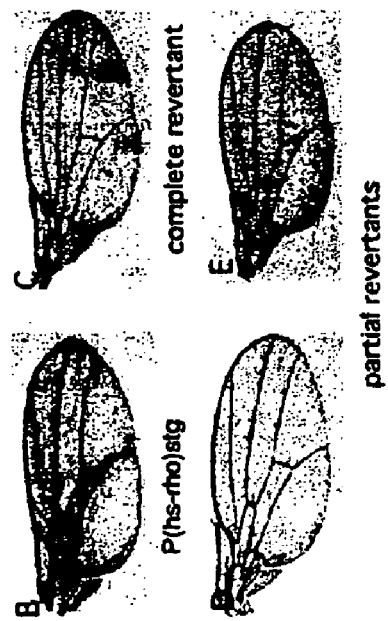
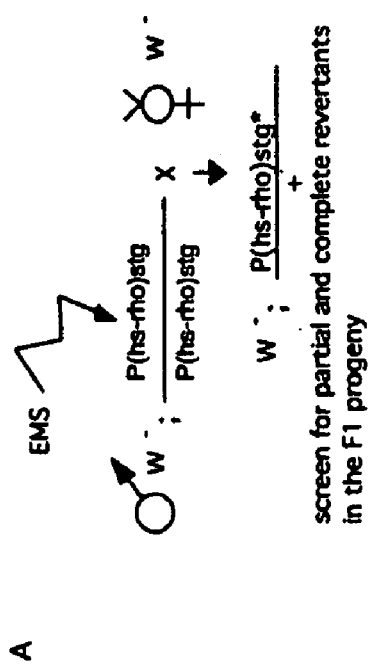
FIGS. 5A, 5B, 5C, 5D, 5E
FIG. 5

FIG. 5F

```
                                                                                        LCC              CNF
                                                                                         ↓               DNT
                                                                                                          ↓
             1       -15 16           30 31           45 46           60 61           75 76           90
1  H-RhoA    MAAIRKKLVIVGDGA CGKTCLLIVFSKDQF PEVYVPTVFENYVAD IEVDGKQVELALWDT AGQEDYDRLRPLSYP DTDVILMCFSIDSPD  90
2  H-RhoC    MAAIRKKLVIVGDGA CGKTCLLIVFSKDQF PEVYVPTVFENYVAD IEVDGKQVELALWDT AGQEDYDRLRPLSYP DTDVILMCFSIDSPD  90
3  D-Rho1    MTTIRKKLVIVGDGA CGKTCLLIVFSKDQF PEVYVPTVFENYIAD IEVDGKQVELALWDT AGQEDYDRLRPLSYP DTDVILMCFSIDSPD  90
4  H-RhoB    MAAIRKKLVVVGDGA CGKTCLLIVFSKDEF PEVYVPTVFENYVAD IEVDGKQVELALWDT AGQEDYDRLRPLSYP DTDVILMCFSVDSPD  90
5  D-Rac1    --MQAIKCVVVGDGA VGKTCLLISYTTNAF PGEYIPTVFDNYSAN VMVDAKPINLGLWDT AGQEDYDRLRPLSYP QTDVFLICFSLVNPA  88
6  D-Rac2    --MQAIKCVVVGDGA VGKTCLLISYTTNAF PGEYIPTVFDNYSAN VMVDAKPINLGLWDT AGQEDYDRLRPLSYP QTDVFLICFSLVNPA  88
7  H-Rac2    --MQAIKCVVVGDGA VGKTCLLISYTTNAF PGEYIPTVFDNYSAN VMVDSKPVNLGLWDT AGQEDYDRLRPLSYP QTDVFLICFSLVSPA  88
8  H-Rac3    --MQAIKCVVVGDGA VGKTCLLISYTTNAF PGEYIPTVFDNYSAN VMVDGKPVNLGLWDT AGQEDYDRLRPLSYP QTDVFLICFSLVSPA  88
9  D-Cdc42   --MQTIKCVVVGDGA VGKTCLLISYTTNKF PSEYVPTVFDNYAVT VMIGGEPYTLGLFDT AGQEDYDRLRPLSYP QTDVFLVCFSVVSPS  88

91     105 106          120 121          135 136          150 151          165 166          180
1  H-RhoA    SLENIPEKWTPEVKH FCPNVPIILVGNKKD LRNDEHTRRELAKMK QEPVKPEEGRDMANR IGAFGYMECSAKTKD GVREVFEMATRAALQ 180
2  H-RhoC    SLENIPEKWTPEVKH FCPNVPIILVGNKKD LRQDEHTRRELAKMK QEPVRSEEGRDMANR ISAFGYLECSAKTKE GVREVFEMATRAGLQ 180
3  D-Rho1    SLENIPEKWTPEVKH FCPNVPIILVGNKKD LRNDPNTIRDLAKMK QEPVKPQEGRAMAEK INAFAYLECSAKSKE GVRDVFETATRAALQ 180
4  H-RhoB    SLENIPEKWVPEVKH FCPNVPIILVANKKD LRSDEHVRTELARMK QEPVRTDDGRAMAVR IQAYDYLECSAKTKE GVREVFETATRAALQ 180
5  D-Rac1    SFENVRAKWYPEVRH HCPSTPIILVGTKLD LRDDKNTIEKLRDKK LAPITYPQGLAMAKE IGAVKYLECSALTQK GLKTVFDEAIRSVLC 178
6  D-Rac2    SFENVRAKWFPEVRH HCPSVPIILVGTKLD LRDDKQTIEKLKDKK LTPITYPQGLAMAKE IAAVKYLECSALTQK GLKTVFDEAIRSVLC 178
7  H-Rac2    SYENVRAKWFPEVRH HCPSTPIILVGTKLD LRDDKTIEKLKEKK  LAPITYPQGLALAKE IDSVKYLECSALTQR GLKTVFDEAIRAVLC 178
8  H-Rac3    SFENVRAKWYPEVRH HCPHTPILLVGTKLD LRDDKDTIERLRDKK LAPITYPQGLAMARE IGSVKYLECSALTQR GLKTVFDEAIRAVLC 178
9  D-Cdc42   SFENVKEKWVPEITH HCQKTPFLLVGTQID LRDENSTLEKLAKNK QKPITMEQGEKLAKE LKAVKYVECSALTQK GLKNVFDEAILAALE 178

181    195 196
1  H-RhoA    ARRGKKKSGCLVL-- 193
2  H-RhoC    VRKNKRRRGCPIL-- 193
3  D-Rho1    VKKRKKTRCLLL--- 192
4  H-RhoB    KRYGSQNGCINCCKV L 196
5  D-Rac1    PVLQPKSKRKCALL- 192
6  D-Rac2    PVRGPKRHKCALL-- 192
7  H-Rac2    PQTROOKRACSLL-- 192
8  H-Rac3    PPVKKPGKKCTVF-- 192
9  D-Cdc42   PPEPTKKRKCKFL-- 191
```

METHOD FOR GENERATING OVEREXPRESSION OF ALLELES IN GENES OF UNKNOWN FUNCTION

CROSS REFERENCE TO RELATED APPLICATIONS

This application is a divisional application of U.S. application Ser. No. 10/263,367 filed Oct. 1, 2002, now issued as U.S. Pat. No. 7,193,126; which claims the benefit under 35 USC § 119(e) to U.S. Application Ser. No. 60/326,546, filed Oct. 1, 2001, now abandoned. The disclosure of each of the prior applications is considered part of and is incorporated by reference in the disclosure of this application.

GRANT INFORMATION

This work was supported by National Institutes of Health # NS29870 and NSF # NSFIBN-9604048.

BACKGROUND OF THE INVENTION

1. Field of the Invention

The present invention generally concerns procedures for generating transgenic flies for expression and study of a gene of interest. The invention particularly concerns processes for generating and using stocks of transgenic *Drosophila* that carry a mutant allele of a gene of unknown function related to the production of a new dominant phenotype, as well as methods for utilizing transgenic *Drosophila* to generate and study other genes, such as those encoding dominant-negative bacterial toxins.

2. Description of Related Art

Pharmacological research is hampered by the labor-intensive and extremely lengthy identification and systematic characterization procedures for new therapeutic compounds. A conventional process involves the screening of Thousands of individual compounds there are conventionally screened for a desired biological therapeutic benefit. Less than 1 in 10,000 of the synthetic compounds screened have ultimately been approved by the Food and Drug Administration. The cost approximates $200+ million per drug put into service. Natural products have provided the impetus for search of therapeutically effective pharmacological compounds for many years. Complex mixtures derived from cells, or their metabolites, are screened for biological activity, and the specific molecule possessing the activity is purified using the biological activity as the means for identifying the component of the mixture possessing the desired activity.

An alternative methodology has been to screen previously synthesized individual compounds saved in "libraries" in drug companies or research institutions. More recently, peptide or oligonucleotide libraries have been developed which may be screened for a specific biological function.

Because many of the existing therapeutics have been identified accidentally, their mechanism of action is not well understood. A more effective approach to identifying new molecular compounds effective against various disease conditions requires precise knowledge of the molecular defect underlying a given disease, and of the cellular pathways and processes of action. This is a weakness inherent in the current screening methodologies of compound libraries employing cell-free and in vitro cell-based assays.

It should also be noted that high throughput screening does not actually identify a drug, but merely high-quality "hits" or "leads" that are active at a relatively low concentration. This powerful screening tool also suffers from a number of limitations like bioavailability, toxicity and specificity. Subsequent studies are required before such a compound metamorphosizes into a therapeutically useful drug.

Screening of compound libraries with cell-free and in vitro assay systems has intrinsic limitations and weaknesses. For example, in cell-free systems, screening is limited to single target molecules, and they do not provide an inherent test for either specificity of the interaction, or of the toxicity of the test compound. But, perhaps most importantly, cell-free systems do not identify intermediary targets in signaling pathways made up of a hodge-podge of cell membrane, cytoplasmic, and nuclear-based components not present in cell-free systems.

Cell-based assays have several advantages over cell-free systems, the first being the capacity of self-replication. Moreover, the interactions occur in a biological context hopefully more closely mimicking the normal physiological conditions in vivo. Bioavailability and cytotoxicity are more easily assessed, but they often provide inadequate similarity to the in vivo disease conditions developing in multicellular tissues.

With the current screens using cell-free or in vitro cell-based assays, these differentiation end-points are difficult to assess and cell number or cell mass may be the more appropriate assay for their high-throughput designs. This is due to the fact that current screening methodologies can not easily discriminate growth arrest due to differentiation from other antiproliferative or simple cytotoxic effects.

Whole embryo cultures have also been used to screen for chemical effects in, for example, rodents and chickens. Adverse embryonic outcomes (malformations or embryotoxicity) are directly related to the serum concentration of the compound being tested. These serum concentrations can be directly compared to the serum concentration in the human. Whole embryo culture systems are problematic in that they result in large numbers of in vivo false-positives, and development within the cultures is limited to the very early stages of embryogenesis.

Similarly, the nematode *C. elegans* is frequently utilized as a model organism for the genetic dissection of developmental controls and cell signaling. However, in *C. elegans* there are no genetically sensitized systems available that permit reliable detection of even a two-fold reduction in a signaling process caused by either a chemical compound or a mutation in a gene. Although *C. elegans* can be grown in microtiter plates, the phenotypic screens are markedly limited. Also, chemical compounds would necessarily be administered by feeding, and would thus possess all of the aforementioned inherent disadvantages.

Another widely-utilized model genetic system is yeast. Although yeast are easily maintained and can readily be grown in large numbers, they are a simple, single-celled organism and thus possess the inherent limitation of being incapable of replicating a complex, multi-cellular system. Although the yeast system offers a comparatively higher throughput, it possesses inherent limitations, as most disease conditions are dependent upon cell-cell interactions within tissues that cannot be modeled in yeast. Finally, and most importantly, the overall degree of conservation of signaling pathways between yeast and human is significantly lower than that between *Drosophila* and humans.

Studies in the fruit fly *Drosophila melanogaster* have altered our estimate of the evolutionary relationship between vertebrate and invertebrate organisms. Key molecular pathways required for the development of a complex animal, such as patterning of the primary body axes, organogenesis, wiring of a complex nervous system and control of cell proliferation have been highly conserved since the evolutionary divergence of flies and humans. When these pathways are disrupted in either vertebrates or invertebrates, similar defects are often observed. The utility of *Drosophila* as a model organism for the study of human genetic disease is now well documented. Developmental defects such as the mesenchymal malformations associated with Saethre-Chotzen syndrome (Howard et al. 1997), formation of intracellular inclusions in polyglutamine-tract repeat disorders such as spinocerebellar ataxia and Huntington disease (Fortini and Bonini 2000), and loss of cellular-growth control and malignancy resulting from mutations of tumor suppressor genes (Potter et al. 2000) have been analyzed effectively using *Drosophila* as the model genetic system. The many basic processes that are shared between *Drosophila* and humans, in conjunction with the recent completion of the *Drosophila* genomic sequence, provide the necessary ingredients for launching systematic analyses of human disease-causing genes in *Drosophila*.

The value of *Drosophila* as a screening system for evaluating the biological activities of chemicals has been well documented (see e.g., Schulz, et al, 1955. Cancer Res. 3(suppl.): 86-100; Schuler, et al., 1982. Terat. Carcin. Mutag. 2:293-301). Small numbers of chemical substances are administered to larvae or flies by feeding, and flies are then analyzed for survival and for phenotypic alterations. Although these conventional tests show the potential use of *Drosophila* as a tool to analyze the function of small molecular weight compounds, these methods neither permit high-throughput screens, nor permit the directed search for small molecular weight compounds that interfere with a specific morphogenetic pathway related to a human disease condition. Application of compounds by feeding requires relatively large amounts of the substance, and its uptake by the larvae and thus its final concentration is, at best, difficult to control. Furthermore, application by feeding does not permit automation of the procedure necessary for high-throughput analysis (Ernst Hafen, United States Patent Application, 20020026648).

The *Drosophila* epidermal growth factor (EGF)-receptor tyrosinekinase (EGF-R) controls a large array of cell-fate choices throughout the life cycle (Schweitzer, R. & Shilo, B. Z. (1997), Perrimon, N. & Perkins, L. A. (1997)) and can be activated by multiple ligands (Moghal & Sternberg (1999)). Among them, Vein is directly secreted to signal to adjacent cells (Schnepp, et al (1996)), whereas other EGF ligands such as Spitz (Spi) (Rutledge, et al (1992)) and Gurken (Grk) (Neuman-Silberberg & Schupbach (1993)) are similar to the human transforming growth factor a and are initially expressed as membrane-bound precursors. Numerous studies have provided corroborating evidence that these latter precursor ligands are initially inert and depend on two accessory membrane proteins, Rhomboid (Rohr) and Star, to be processed into active diffusible forms (Schweitzer et al (1995); Guichard Et Al (1999); Pickup & Banerjee (1999); Guichard Et Al (1999); Bang & Kintner (2006); Guichard Et Al (2000); Lee Et Al (2001); Urban Et Al (2001); Golembo Et Al (1996)). Rho is a predicted seven-pass transmembrane protein (Bier et al (1990)), and Star is predicted to be a type II single-pass transmembrane protein predominantly localized in the endoplasmic reticulum (ER) (Pickup & Banerjee (1996); Kolodkin et al (1994)), which acts as an obligate partner of Rho to activate EGF-R signaling in a cell nonautonomous fashion (Bier et al (1990)). Recent studies show that Star is necessary for Spi to translocate from the ER to the Golgi apparatus, where it is directly cleaved by Rho, a novel type of intramembrane serine protease (Lee Et Al (2001); Urban Et Al (2001); Tsruya et al (2002)). Unlike the Egf-r, spitz (spi), and Star genes, which are expressed ubiquitously in most epidermal cells, rhomboid (rho) is expressed in a highly localized and dynamic pattern (Bier et al (1990)) that correlates with the in situ activation pattern of mitogen-activated protein kinase (MAPK), an essential downstream component of all tyrosine kinase receptors (Gabay et al (1997) *Science* 277; Gabay et al (1997) *Development* 124; Bier (1998)). This latter observation suggests that Rho provides the appropriate restricted spatial and temporal activation for membrane-bound EGF ligands. A good example of the localized activity of Rho is provided by the wing disc, in which the restricted expression of rho in longitudinal stripes controls the commitment of these cells to the vein fate through the activation of EGF-RMAPK signaling. Thus, rhove mutants, who fail to express rho in vein primordia, lack sections of veins, whereas ubiquitous ectopic expression of rho converts the entire wing blade into a single solid vein (Bang & Kintner (2000); Lindsley, D. & Zimm (1992); Sturtevant et al (1993)).

Current methods for generating gain-of-function mutations are of two general sorts.

1) Structure/function studies in which mutant forms of a gene-x are created in vitro by one of a several of existing methods for making site directed mutations and then introduced into an organism to assay the function of the mutated gene.

2) Systematic screens for mutant alleles of the endogenous gene-x using one of a variety of mutagens.

These two types of analysis are typically very labor intensive and can only recover rather limited numbers of mutations. For example, in the case of Inventors' structure/function analysis of the *Drosophila* sog gene, one person spent approximately two years generating a collection of 23 mutant forms of the gene, which were then transformed into flies to obtain several independent transgenic lines of flies carrying each construct. These mutant sog constructs were then misexpressed in the wing to test for the function of the mutated genes. Using this approach Inventors identified two activities of Sog which had not been previously known. Thus, whereas misexpression of wild-type sog during wing development causes a mild loss-of vein phenotype (FIG. 1C; Yu et al., 1996), misexpression of one mutant truncated form of sog— referred to as supersog—generates more severe wing patterning defects (FIG. 1D; Yu et al., 2000), while misexpression of a second truncated form induces production of ectopic wing veins (Yu et al., manuscript in preparation). Inventors and other investigators have also conducted several different systematic screens for mutations in the endogenous sog gene, which cumulatively amounted to at least one year of work by a single person. These tedious screens lead to the isolation of only null and partial loss-of-function sog alleles (Wieschaus et al., 1984; Ferguson et al., 1992; Francois et al., 1994).

What is needed is a method that could be employed to generate dominant alleles of a wide range of genes using various mutagens to provide insight to the function and mechanism of action of novel genes. This approach should be of particular utility in investigating the function of human disease genes, which have no known functional motifs but have homologues in *Drosophila* (Reiter et al (2001)). Furthermore, the method should be applicable to any organism in which it is possible to misexpress transgenic constructs at high levels in a conditional fashion.

SUMMARY OF THE INVENTION

The primary object according to this invention is to provide a genetic method for generating a novel overexpression activity allele (hereinafter "NOVA") of a gene of interest. Novel overexpression activity alleles of a gene of unknown function can be powerful genetic tools that can provide important insights into the function of that gene.

Another object according to this invention resides in the ability to, once a NOVA allele of a gene has been isolated, design mutant screens to identify second-site mutations in other genes acting in the same pathway as the gene of interest. Mutants in these second-site modifier loci alter the NOVA phenotype, either by enhancing or suppressing that phenotype.

Still another object according to this invention is the potential use of mutagens to revert NOVA mutant phenotypes generated by this method, and thereby efficiently generate second-site intragenic loss-of-function alleles within the gene of interest for structure/function studies and designing therapeutics for human diseases.

In accordance with these objects, this invention contemplates a method for generating, in virtually any organism, a novel overexpression activity (NOVA) allele of a gene (gene-x) of unknown function. The method comprises misexpressing a wild-type copy of a gene by known methods, determining the phenotypic consequence of the misexpressing, namely transgene-x, and mutagenizing male organisms carrying this transgene-x. The mutants, for example Drosophila males, are mated en masse to relevant female strains, thereby activating global or restricted expression. The progeny are screened for new NOVA dominant phenotypes resulting from the expression, and these NOVA mutant progeny are crossed to appropriate balancer females to establish stable stocks. The NOVA dominant phenotypes resulting from the expression can be in constitutively active or dominant negative form.

It is also contemplated by this invention that any organism that can be misexpressed and overexpressed is a candidate for this method. Most preferably, the organism is Drosophila. The mutagenizing contemplated herein may be accomplished with chemical mutagens, for example, ethane methyl sulfonate, an alkylating agent highly effective in eucaryotic systems. The mutagenizing can also be accomplished with radiation, or any other factor capable of causing point mutation. Point mutations are preferable because they allow precise targeting. They may be targeted at random sites in a particular region of DNA, or at a particular base pair.

The mutagenizing can also be accomplished with broadly functioning mutagens. Highly preferred methods contemplated by this invention cause mutations enzymatically, preferably with the enzyme transposase. The enzymic mutagenizing agent preferred in this invention is p-element Transposase, most preferably, Δ2-3 Sb/TM6 Transposase.

Another, most preferred, embodiment in accordance with this invention is a method for generating novel mutations in human genes. Hereinagain, the method involves the misexpressing of a wild-type copy of a gene by known methods, and determining the phenotypic consequence of the misexpressing, namely transgene-x. The method further involves mutagenizing male flies carrying the transgene-x, activating global or restricted expression by mating en masse to relevant female strains and screening progeny for NOVA dominant phenotypes resulting from the expression. The NOVA mutants are then crossed to appropriate balancer females to establish stable stocks. The misexpressed wild-type copy can be one of approximately 1000 human disease genes currently identified in Drosophila.

A more specific and most preferred embodiment of this invention is a method for generating dominant-negative forms of bacterial toxins using NOVA screens in Drosophila, employing the following steps. The first contemplated step involves creating transgenic flies able to express a bacterial toxin using the UAS/GAL4 conditional expression system. This is done by preparing DNA encoding full-length bacterial toxin (e.g. from genomic clone, plasmid subclone, or by PCR), inserting the toxin-encoding gene into the pUAS-vector, transforming into E. Coli DH5α, and testing for successful recombinants. Next, the w+ marked pUAS-toxin DNA is purified and injected into w− fly embryos. F1 generation w+ transformants are isolated and balanced, transformed pUAS-toxin lines are established. These lines are capable of expressing UAS-toxin in specific tissues, using a set of GAL lines to generate viable phenotypes (e.g. wingless or eyeless phenotypes).

The second contemplated step involves determining whether the Drosophila toxin phenotype is caused by the same mechanism as in human cells by analyzing the phenotype at the cellular level in third instar larvae cytoskeleton for toxins affecting Rho-like GTPases, For Cytolethal Distending Toxins, this is preferably done by testing the reorganization of actin to determine the shape and size of the cells. For LF of B. anthracis, determination is preferably accomplished by testing the activity of MAPK, for example, using anti-diphosphoMAPK antibody. Preferably, testing the activity of Adenyl cyclase is also performed for EF of B. anthracis. All toxins are tested for capability of inducing cell-lethality, and whether said lethality occurs through apoptosis or necrosis.

Preferably, genetic epistatsis experiments are used to confirm that the cellular targets of the toxin are fly homologues of the human targets. This is accomplished by testing to determine if the toxin-induced phenotype is modified in a heterozygous mutant background for the predicted targets and for their known partners, more preferably screening for enhancers of the toxin, and most preferably also performing a phenotype analysis to identify such targets when the cellular target is not known.

The third contemplated step involves analyzing the effect of the novel dominant-negative toxins by establishing a mutant line carrying the UAS-toxinDN, determining what effect the toxinDN has when expressed alone, determining by PCR what lesion has been created in the UAS-toxin insertion and the corresponding altered protein sequence, and cloning a mutant toxinDN gene into a fresh pUAS vector to obtain a construct. The construct is transformed into flies and expressed in toxinDN gene flies with GAL4. The final step is confirming that this is the only mutation required for DN toxin activity.

The advantages of the method according to this invention over existing methods are the efficiency and speed with which it can be applied to a wide variety of genes. Moreover, because the method is not predicated on assumptions based on protein domain structure and function, mutants can be recovered in an unbiased fashion.

Still further objectives, embodiments and advantages of the invention will become apparent to those skilled in the art upon reading the entire disclosure contained herein.

Figure 1:
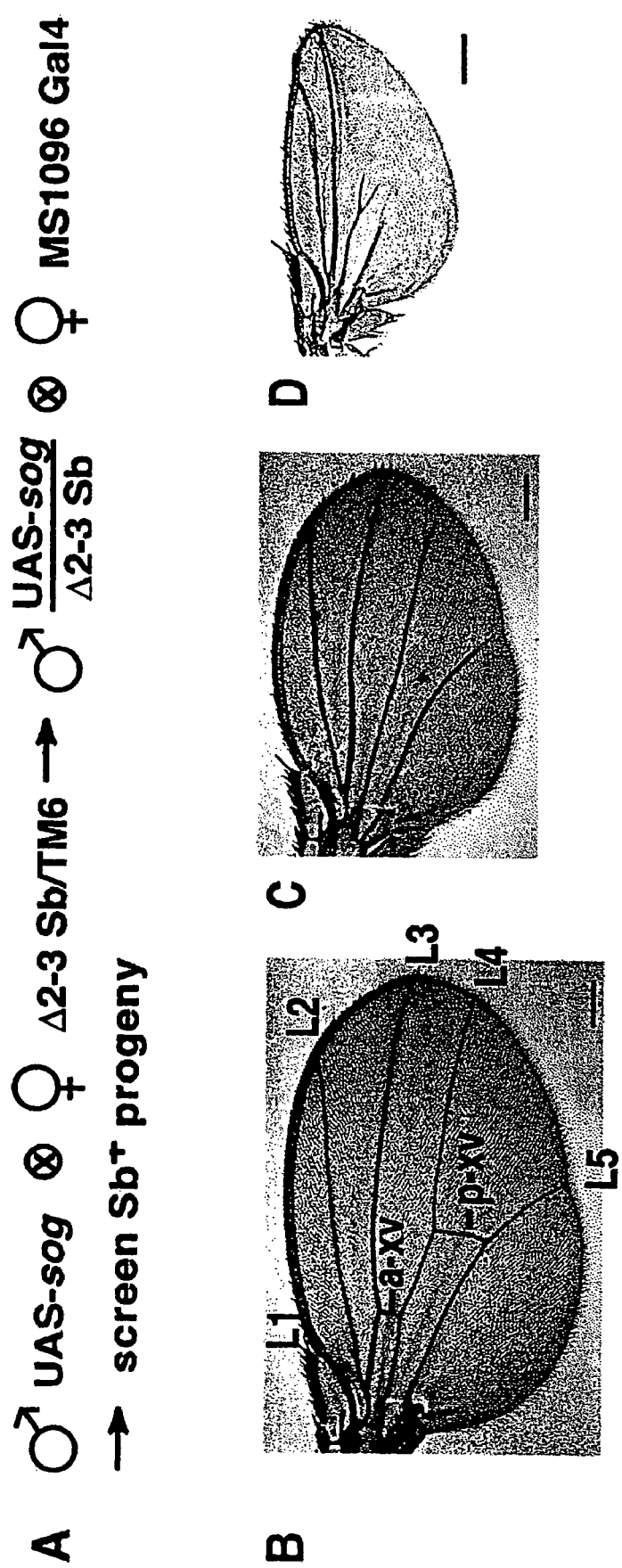
FIG. 1 shows a genetic scheme for generating and screening for NOVA sog mutants. A) This crossing scheme is an example of a NOVA screen using a full length UAS-sog transgene as the target. Sog functions by inhibiting the activity of BMP related ligands (François et al, 1994; Yu et al., 2000). B) A wild-type fly wing with the longitudinal veins (L1-L5) and the anterior and posterior cross-veins (a-xv and p-xv respectively) are indicated. C) In previous studies (Yu et al., 1996; Yu et al., 2000) Inventors determined that misexpression of full length Sog throughout the wing primordium of developing larvae and pupae using a ubiquitous GAL4 source (MS 1096-GAL4=Ubi-GAL4) results in a very mild vein-loss phenotype in which cross-veins and distal tips of the L4 and L5 veins are missing (compare to 1B). D) Misexpression of a truncated form of Sog (Supersog) causes a much more severe wing phenotype in which wing veins fuse (e.g. L2 to L3 and L4 to L5), vein tissue is lost, and the wing is smaller in overall size (Yu et al., 2000).
Figure 2:
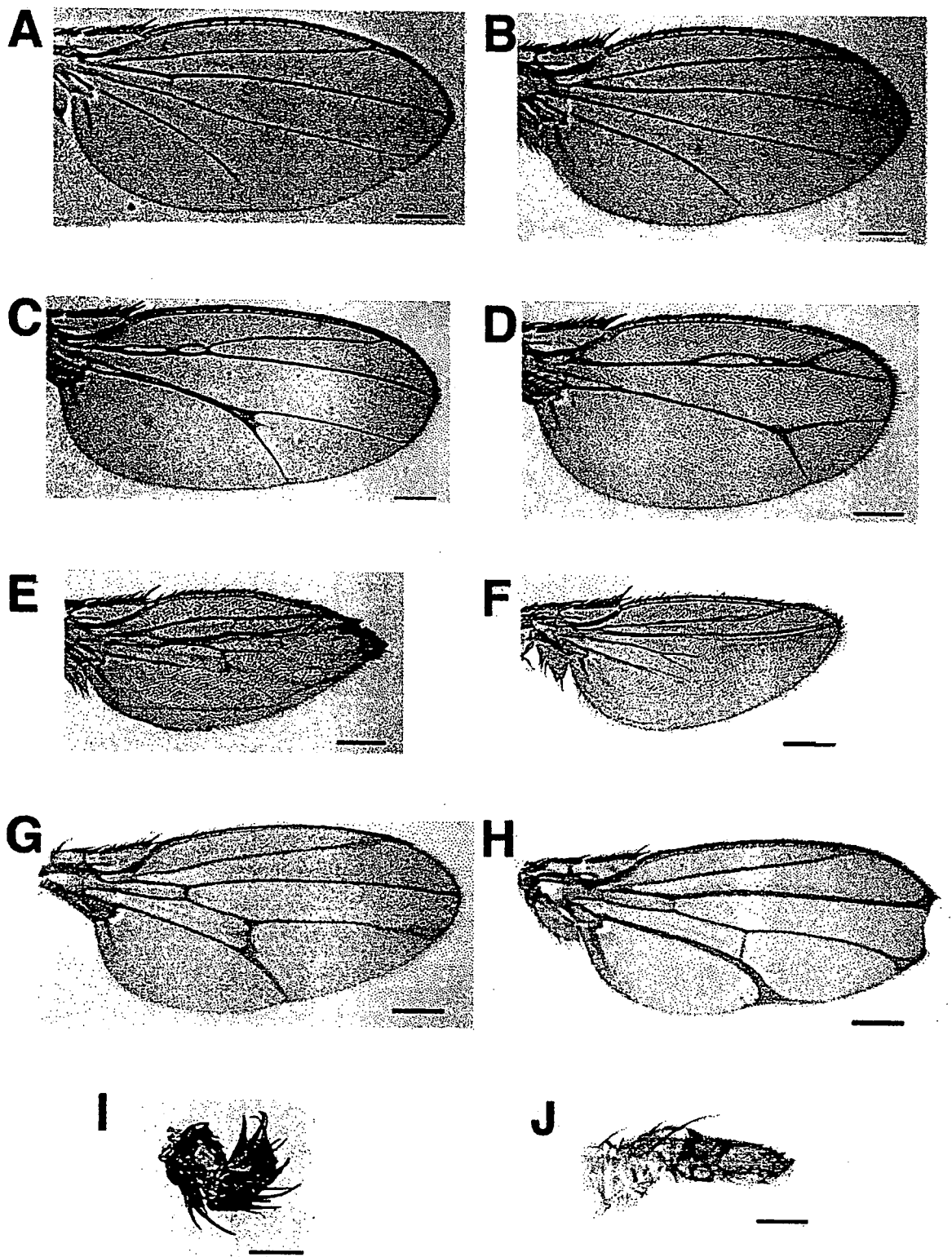

FIG. 2 is a comparison of NOVA sog alleles with loss-of-function mutations in gene encoding components of the BMP signaling pathway. Novel NOVA sog alleles isolated from the genetic scheme depicted in FIG. 1 generate wing phenotypes when misexpressed during wing development that are similar to those resulting from loss-of-function mutations in gene encoding components of the BMP signaling pathway. A) A mutant wing from an individual with reduced activity of the BMP ligand encoded by the glass-bottom boat (gbb) gene. B) Ubiquitous misexpression of a full length UAS-sog transgene results in a phenotype very similar to that of a loss-of-function gbb mutant (panel A). C) A mutant wing from an individual with reduced activity of the BMP ligand encoded by the decapentaplegic (dpp) gene in which wing veins fuse (e.g. L2 to L3 and L4 to L5). D) A wing misexpressing a truncated UAS-sog1 transgene (UAS-supersog1), which was generated by in vitro mutagenesis, in the same cells that normally express the dpp gene. Note how similar this phenotype is to that of a loss-of-function dpp mutant (panel C). E) Ubiquitous misexpression of the UAS-supersog1 transgene results in a wing phenotype in which veins fuse (e.g. L2 to L3 and L4 to L5), vein tissue is lost, and the wing is smaller in overall size. F) Ubiquitous misexpression of the UAS-sog*5-73 mutant which was generated using the genetic crossing scheme depicted in FIG. 1 results in a phenotype that is nearly identical to that generated by the in vitro created UAS-supersog1 (compare with panel E). G) A viable partial loss of function mutant in the type-I BMP receptor encoded by the thick veins (tkv) gene results in thickened veins as a consequence of defects in lateral inhibitory signaling during pupal development. H) Ubiquitous misexpression of the UAS-sog*5-8 mutant results in a thickened vein phenotype that is very similar to that observed in tkv mutants (compare with panel G). I) Severe reduction in dpp function during wing development results in a failure of wing outgrowth. J) Ubiquitous misexpression of the UAS-sog*5-2 mutant results in greatly reduced wing size similar to that observed in the wings with greatly reduced Dpp activity (compare with panel I).

FIG. 3 depicts a molecular analysis of NOVA sog mutants. A) Diagram of the Sog protein. Sog is a large extracellular protein (1038 amino acids) consisting of four cysteine rich domains (CRs) defined by a conserved pattern of 10 cysteine residues. The first CR domain is located near the N-terminus of the protein and is separated by a long spacer from the remaining three CRs that are clustered at the C-terminus. B) Immunoblot analysis of proteins extracted from flies carrying the full length UAS-sog construct or various mutant forms (UAS-sog*) under the control of HS-GAL4. Protein extracts were prepared from flies with (+) or without (−) heat induction. Truncated forms of the Supersog protein are produced from several of these mutants including the supersog-like mutant sog*5-73 (FIG. 3F) and the more severe mutant sog*5-2, which causes a great reduction in wing size (FIG. 3J).

FIG. 4 demonstrates generation of dominant negative EGF-Receptor mutants. Inventors employed a genetic scheme similar to that shown in FIG. 1A for mutagenizing a UAS-EGFR transgene using Δ2-3 transposase as the mutagen in a small scale pilot screen and recovered two dominant negative mutants, one of which is shown here (DN-EGFR2).

All UAS-transgenes were expressed ubiquitously using the MS-1096 GAL4 source (abbreviated G4 in this and subsequent figures). Inventors also conducted a small scale screen using EMS as the mutagen and recovered one mutant (DN-EGFR3). In general, males (M) are more severely affected than females (F) due to dosage compensated expression of the X-chromosome linked MS-1096 GAL4 source. A) A wild type wing. B) A wing in which a wild-type UAS-EGFR transgene is expressed ubiquitously. Note the presence of ectopic wing veins. C) A wing mis-expressing a UAS-rho transgene. rho promotes high levels of EGF-R signaling and therefore generates a very strong ectopic vein phenotype in which most wing cells adopt the vein fate. D) A female wing expressing the classic dominant negative form of EGFR (UAS-DN-EGFR), which is an in vitro generated construct that is truncated a short distance following the transmembrane (TM) domain (see middle row of panel P). In contrast to expression of wild-type EGF-R, expression of DN-EGFR results in vein loss, which is particularly acute for odd numbered veins, which form predominantly on the dorsal surface of the wing where GAL4 expression is strongest. E) A female wing expressing the UAS-DN-EGFR2 mutant generated in the Δ2-3 NOVA genetic screen. This mutant phenotype is very similar to that resulting from expression of the classic DN-EGFR (compare to panel D). The precise nature of the lesion in the DN-EGFR2 mutant, which has been determined by PCR amplification of the mutated transgene and DNA sequencing (bottom row of panel P), results from a deletion of EGFR coding sequences beginning at a site very near that used in creating the classic DN-EGFR construct, which is then fused out-of-frame to part of the white gene. Consistent with this predicted protein structure for DN-EGFR2, a truncated EGFR band on immunoblots of fly protein extracts prepared from DN-EGFR2 expressing flies was observed. F) A female wing expressing the UAS-DN-EGFR3 mutant generated in the EMS NOVA genetic screen. This phenotype is noticeably weaker than that caused by the classic DN-EGFR or DN-EGFR2 (compare with panels D and E). G) A male wing expressing the classic UAS-DN-EGFR mutant. This phenotype is stronger than that observed in females carrying a single copy of the X-linked MS 1096-GAL4 driver (compare to panel D). H) A female wing carrying two copies of the X-linked MS 1096-GAL4 driver expressing the UAS-DN-EGFR2 mutant. This phenotype is approximately equal to that of males expressing a single copy of the GAL4 source, which is significantly stronger than that of females carrying a single copy of the GAL4 driver (compare to panel E). I) A male wing expressing the UAS-DN-EGFR3 mutant. This phenotype is stronger than that observed in females carrying a single copy of the X-linked MS 1096-GAL4 driver (compare to panel F). J) A wing co-expressing the classic DN-EGFR and wild-type EGFR constructs. DN-EGFR prevails in this situation (compare to panels B, E). K) A wing co-expressing the DN-EGFR2 and wild-type EGFR constructs. EGFR largely prevails in this situation (compare to panels B3) L) A wing co-expressing the DN-EGFR3 and wild-type EGFR constructs. A novel phenotype is observed in this situation, which consists of a much more severe ectopic vein phenotype than observed with expression of EGFR alone, and a significant reduction in wing size (compare to panels B, F). The results presented in panels A-L suggest that DN-EGFR2 is similar in activity to the classic DN-EGFR, albeit slightly weaker, and that DN-EGFR3 is noticeably weaker than DN-EGFR and DN-EGFR2 and also has an activity that is distinct from the other two mutants (e.g. see panel L). M) (SEQ ID NO:1) Diagram of wild-type UAS-EGFR construct (top line), UAS-DN-EGFR classic (middle line), and UAS-DN-EGFR2

(bottom line) depicting the locations of the p-element ends (arrow heads), the EGFR gene, and the white marker gene.

FIG. 5 demonstrates generation of loss-of-function revertants by EMS mutagenesis in a HS-rho transgene. A) EMS mutagenesis scheme to revert the NOVA ectopic vein phenotype of rho30A flies, which results from constitutive misexpression of a wild-type rho transgene. B) A wing from the rho30A mutant, which has a moderate-strong ectopic vein phenotype. C) A wing from the rho30A* null revertant (class 0) in which the ectopic vein phenotype has been completely eliminated. D) A wing from a strong, but not null, rho30A* loss-of-function revertant (class 1), which has some residual ectopic veins. E) A wing from a moderate, rho30A* loss-of-function revertant (class 3), which has significant residual ectopic vein material. F) A diagrammatic map of Rho indicating the location and nature of all of rho30A* revertant mutations Inventors have recovered and analyzed (SEQ ID NOS 2-6, 7-11, and 12-13, respectively in order of appearance). Mutations are indicated by symbols above each row of the figure as follows: class 0 null mutations (e.g. full reversion of the rho30A ectopic vein phenotype) are represented by an asterisk in row 2, the first and third asterisks appearing in row 4, by the letter D appearing above row 3, and by the letters L and R appearing above row 4; class 1 mutations with a small amount of residual NOVA rho activity are represented by the letters G, H, N, D and K appearing above row 2, the letter L appearing above row 3, the letter Y appearing above row 4, and the second, fourth and fifth asterisks appearing above row 4; class 2 mutations with a moderate degree of residual NOVA rho activity are represented by the letter W appearing above row 2, the letters S, A, G, I C and N appearing above row 3, and the letter D appearing above row 4; and class 3 mutations with significant residual activity, which is clearly less than that resulting from wild-type rho30A phenotype are represented by the letters I and T appearing above row 3, and the letter V appearing above row 4. These loss-of-function mutations tend to fall in TM domains and usually affect residues that have been highly conserved in other Rho-related family members.

Figure 6:
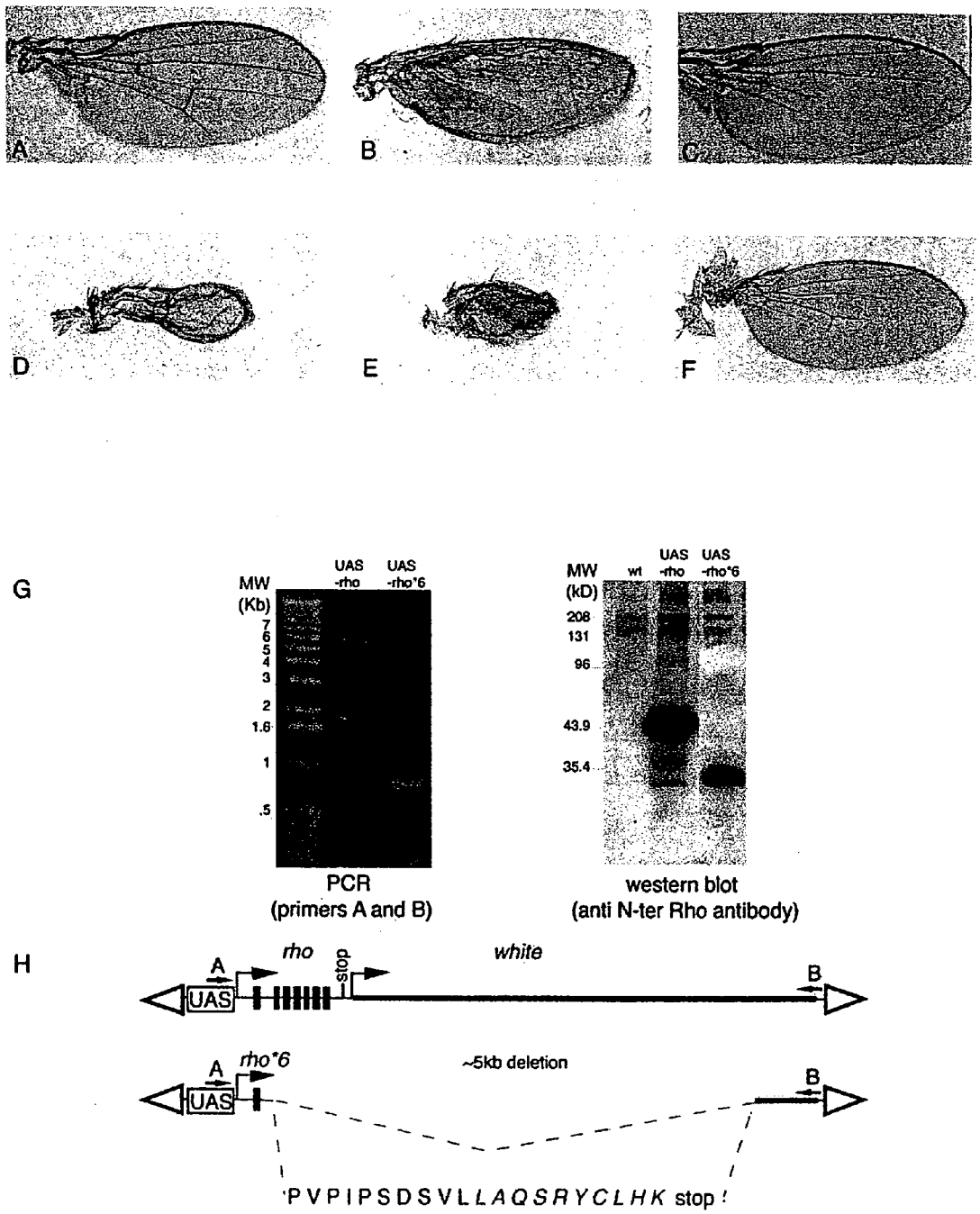

FIG. 6 shows how activated and dominant negative mutants are generated in a UAS-rho transgene. Inventors employed a genetic scheme similar to that shown in FIG. 1A for mutagenizing a UAS-rho transgene using Δ2-3 transposase as the mutagen in a small scale pilot screen and recovered several two NOVA mutants and a dominant negative mutant. A) A wild type wing. B) A wing mis-expressing a UAS-rho transgene, which generates a very strong ectopic vein phenotype. C) A wing from a rho[veinlet] viable loss-of-function mutant in which rho expression is nearly eliminated during larval development. Note that large sections of the distal portions of the L4 and L5 veins are missing as well as the tip of L3. D) A wing from a fly misexpressing the UAS-rho*6 mutant. In addition to being much smaller than a normal wing (panel A) or a wing expressing wild-type rho (panel B), many structures such as innervated bristles are missing from the wing margin. E) A wing from a fly misexpressing the UAS-rho*7 mutant. This wing is much smaller than a typical wing expressing the wild-type rho construct (compare with panel B) and may encode an activated form of Rho. F) A wing from a fly misexpressing the UAS-rho*2 mutant. As this phenotype of this wing is very similar to that of the loss-of-function rho[veinlet] mutant (compare with panel C), this mutant may encode a dominant negative form of Rho. G) Molecular analysis of the rho*6 NOVA rho mutant. The left panel shows DNA products generated from amplification of wild-type versus rho*6 genomic DNA templates using convergent PCR primers located at the ends of the pUAS construct. The band from rho*6 mutants is much smaller than that amplified from wild-type. The right panel shows an immunoblot of protein extracted from flies the expressing full length UAS-rho transgene or the mutant UAS-rho transgene under the control of a heat induced HS-GAL4 driver. As predicted from the PCR and DNA sequencing analysis (see panel H below), the Rho6 protein is highly truncated. H) Diagram comparing the structures of the wild-type starting UAS-rho construct (top line) versus that of the truncated UAS-rho*6 mutant (bottom line) (SEQ ID NO: 14). The conceptually translated Rho*6 mutant protein lacks the last six of seven predicted TM domains and much of the loop between TM1 and TM2. This suggests that sequences near the N-terminus or in TM1 of Rho can interact non-productively with some endogenous factor to generate the resulting NOVA phenotype.

Figure 7:
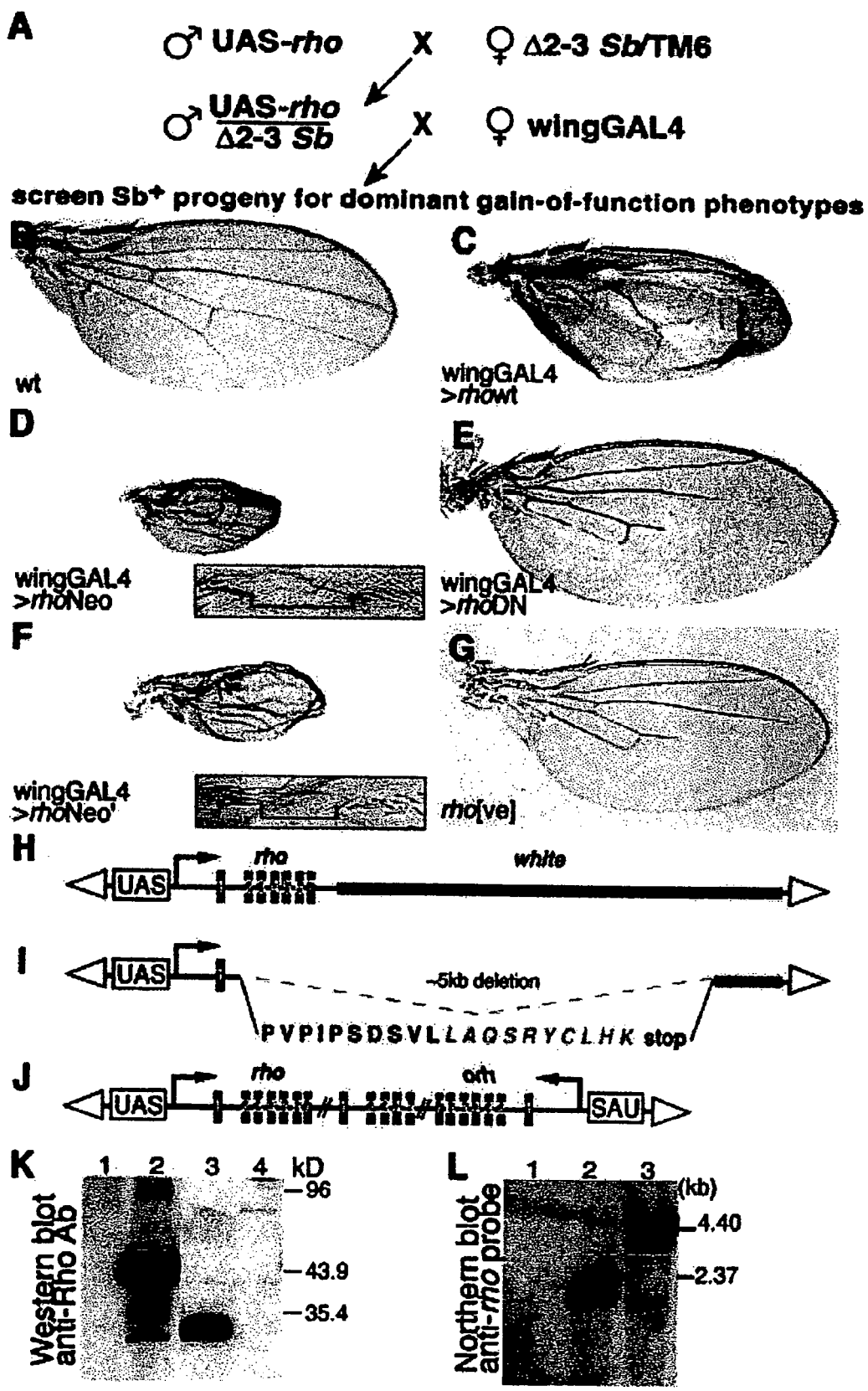

FIG. 7 depicts how a NOVA screen uncovers novel activities of a UAS-rho transgene. A) NOVA mutagenesis scheme. (B-G) Wings of the following genotypes: (B) wild type; (C) wing-GAL4/UAS-rhowt; (D) wing-GAL4/UASrho$^{Neo'}$. Insets here and in F show interrupted margin (bracket) in stronger examples. (E) wing-GAL4AJAS-rho$^{DN}$; (F) wing-GAL4/UAS-rho$^{Neo'}$; (G) rho$^{ve}$. (H-K) Structures of wild-type and mutant pUAS-rho constructs. Solid boxes indicate the transmembrane domains of the Rho protein. Triangles indicate the inverted terminal repeats of the P element. (H) Wild-type pUAS-rho$^{wt}$; (I) pUAS-rho$^{Neo}$(SEQ ID NO: 14); (J) pUAS-rho $^{DN}$; (K) immunoblot analysis of protein extracts from wild-type (lane 1), pHS-rho (lane 2), pHS-GAL4/UAS-rho$^{Neo}$ (lane 3), and pHS-GAL4/UASrho$^{DN}$ (lane 4) adult flies submitted to a 1-h heat shock at 38° C. (L) Northern blot of mRNA extracted from wild-type (lane 1), pHS-GAL 4/UAS-rhowt (lane 2), and pHS-GAL4/UAS-rho$^{DN}$ (lane 3) adult flies following a 1-h heat shock.

Figure 8:
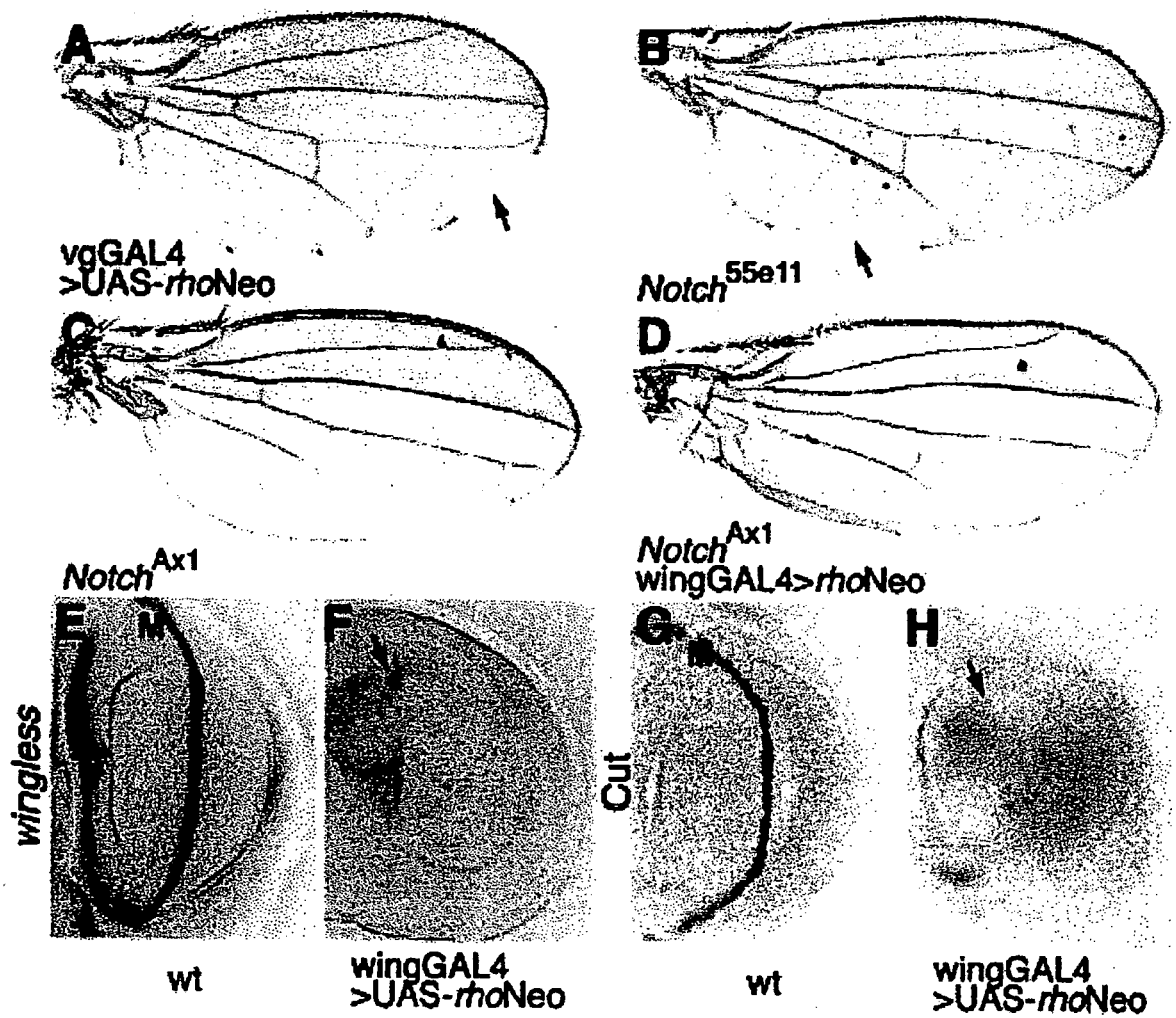

FIG. 8 shows how rho$^{Neo}$ interferes with Notch signaling. (A-D) Wings of the following genotypes: (A) vg-GAL4/UAS-rho$^{Neo}$; (B) N$^{55e11}$/+; (C) N$^{Axl}$/y (male); (D) N$^{Axl}$/+ wing-GAL4/UAS-rho$^{Neo}$ (female); (E) wingless expression along the wing margin (M) of a wild-type third larval instar imaginal disk; (F) absence of wg expression in wing-GAL4/UAS-rho$^{Neo}$ discs (arrow, margin primordium); (G) Cut expression along the wing margin (M) of a third instar imaginal disk; (H) reduced Cut expression in a wing-GAL4/UAS-rho$^{Neo}$ wing disk (arrow, margin primordium).

Figure 9:
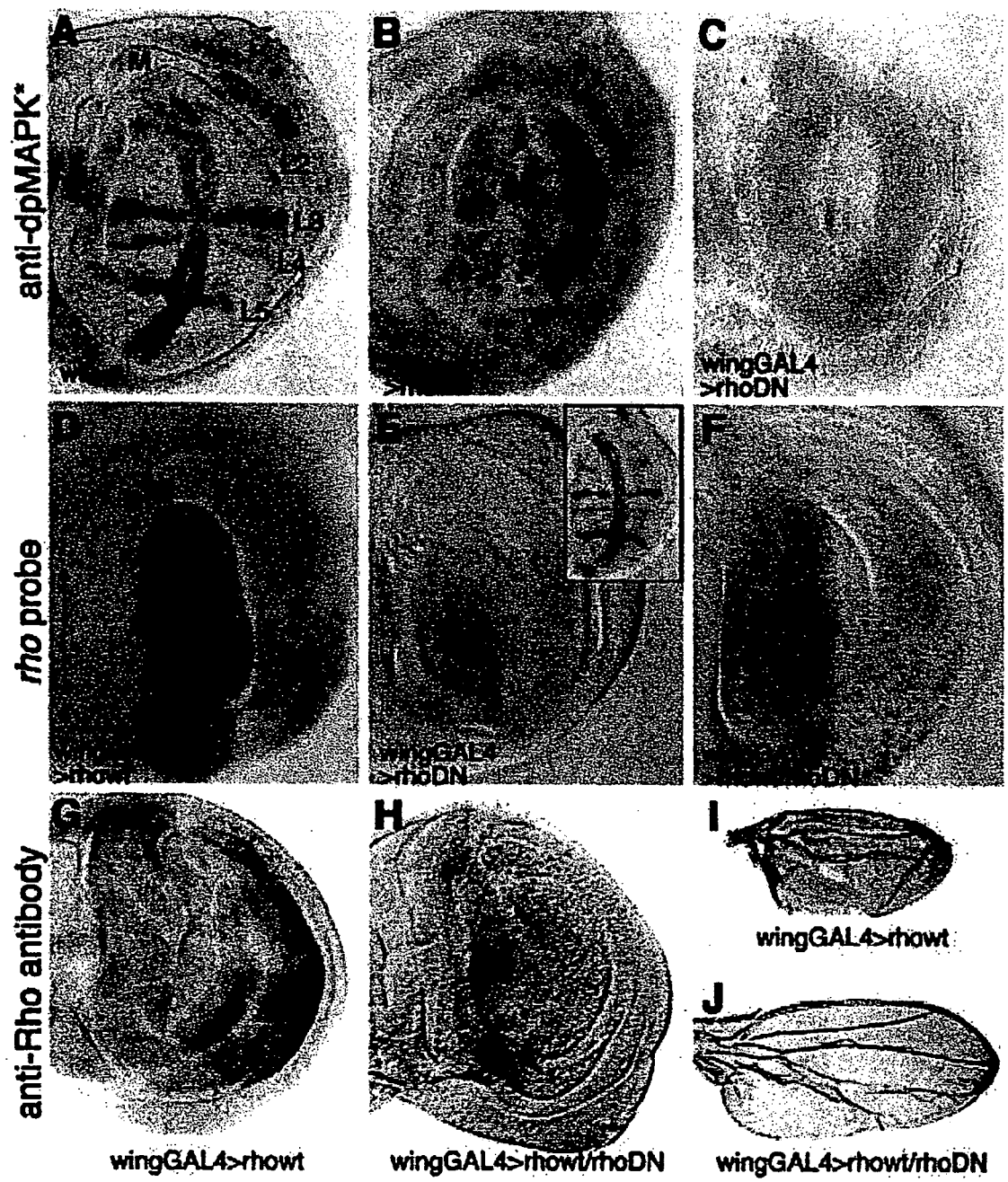

FIG. 9 demonstrates that rho$^{DN}$ functions by an RNAi-like mechanism. (A) MAPK activation in a wild-type third instar imaginal disk in longitudinal vein primordia (L2-L5) and wing margin (M). (B) MAPK activation in a wing-GAL4>UAS-rho$^{wt}$ disk. (C) Lack of MAPK activation in a wing-GAL4>UAS-rho$^{DN}$ disk. (D) rho RNA expression in a wing-GALteUAS-rho$^{wt}$ disk. (E) Undetectable rho RNA expression in a wing-GAL4>UAS-rho$^{DN}$ disk. Endogenous rho expression (Inset) is also lost. (F) rho expression in a wing-GAL4>UAS-rho$^{wt}$/UAS-rho$^{DN}$ disk. (G) Rho protein expression in a GAL4>UAS-rho wing disk. (H) Strong reduction of Rho expression in a wing-GAL4_UAS-rho/UAS-rho$^{DN}$ disk. (I) wing-GAL4>UAS-rho wing. (J) wing-GAL4>UAS-rho$^{wt}$/UAS-rho$^{DN}$ wing.

Figure 10:
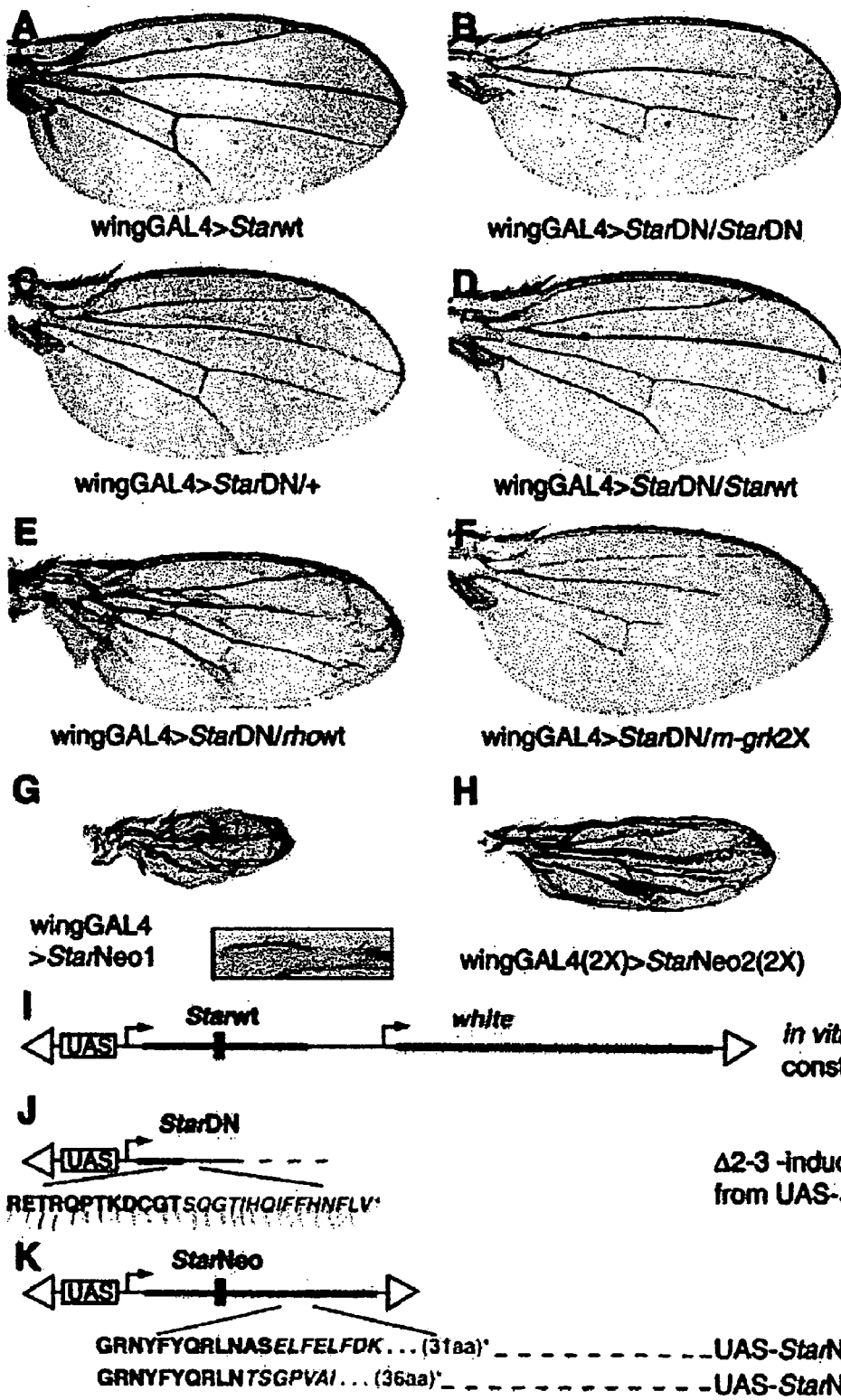

FIG. 10 depicts generation of dominant-negative and $^{Neo}$-morphic Star mutants. (A-H) Wings of the following male genotypes: (A) wing-GAL4>UAS-Star; (B) wing-GAL4>UAS-Star$^{DN}$/UAS-Star$^{DN}$; (C) wing-GAL4>UAS-Star$^{DN}$/+; (D) wing-GAL4>UAS-Star$^{DN}$/UAS-Starwt; (E) wing-GAL4>UAS-Star$^{DN}$/UAS-rhowt; (F) wing-GAL4>UAS-Star$^{DN}$/UAS-m-grk(2×); (G) wing-GAL 4>UAS-Star$^{Neo1}$; (H) wing-GAL4(2×)>UAS-Star$^{Neo2}$/UAS-Star$^{Neo2}$. (I-K) Structure of wild-type and mutant pUAS- Starwt constructs. (I) pUAS-Starwt, the blue box indicates the single transmembrane domain of Star. (J) pUAS-Star$^{DN}$ (SEQ ID NO: 15) a 1.9-kb inversion with breakpoints in both the Star and 3' untranslated simian virus 40 sequences of pUASt results in a C-terminal truncation of the Star protein. (K) pUAS-Star$^{Neo1}$ (SEQ ID NO: 16) and pUAS-Star $^{Neo2}$(SEQ ID NO: 17).

Figure 11:
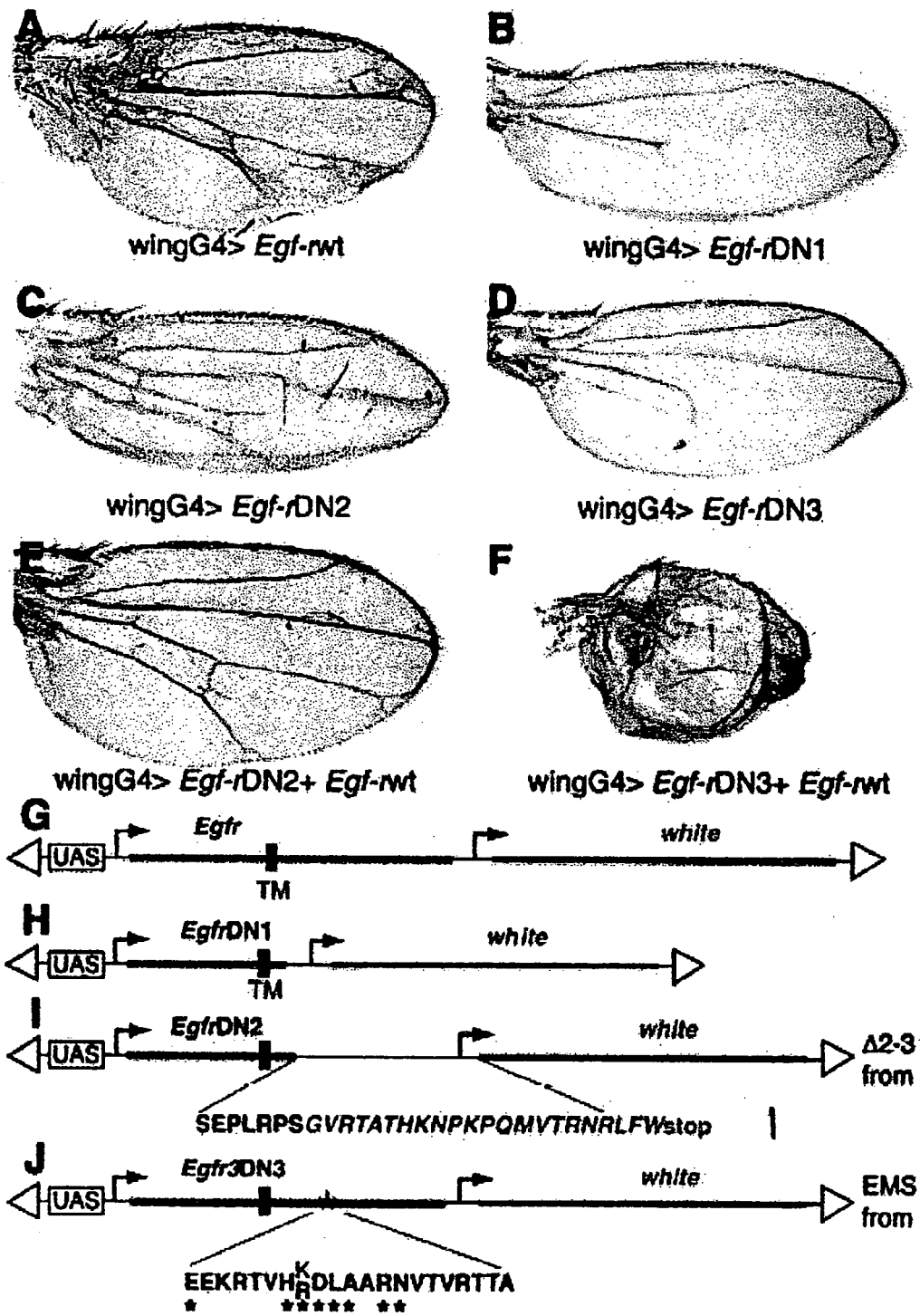

FIG. 11 shows the generation of dominant-negative forms of UAS-Egf-r. (A-F) Wings of the following male genotypes: (A) wing-GAL4>UAS-Egf-r$^{wt}$; (B) wing-GAL4/>E-r$^{DN1}$; (C) wing-GAL4>Egf-r$^{DN2}$; (D) wing-GAL4>Egf-r$^{DN3}$, (E) wing-GAL4>Egf-r$^{DN2}$/Egf-rwt; (F) wing-GAL 4>Egf-r$^{DN3}$/Egf-r$^{wt}$. (G-J) structures of wild-type and mutant pUAS-Egf-r constructs: (G) pUAS-Egf-r$^{wt}$ (H) pUAS-Egfr$^{DN1}$, which has a STOP codon 20 amino acid after the transmembrane domain; (I) pUAS-Egf-r$^{DN2}$, which has a breakpoint mapping 13 amino acid downstream of that of Egf-r$^{DN2}$(SEQ ID NO: 1); (J) pUAS-Egf-r$^{DN3}$, which has a point mutation (R1062K) in the kinase domain (SEQ ID NO: 18). Stars (*) indicate consensus residues conserved across a wide variety of tyrosine kinases.

FIG. 12 shows that many bacterial toxins modify Rho-like GTPases at specific residues, which are conserved in Rho/Rac fly homologues (SEQ ID NOS: 19-27, respectively in order of appearance).

Figure 13:
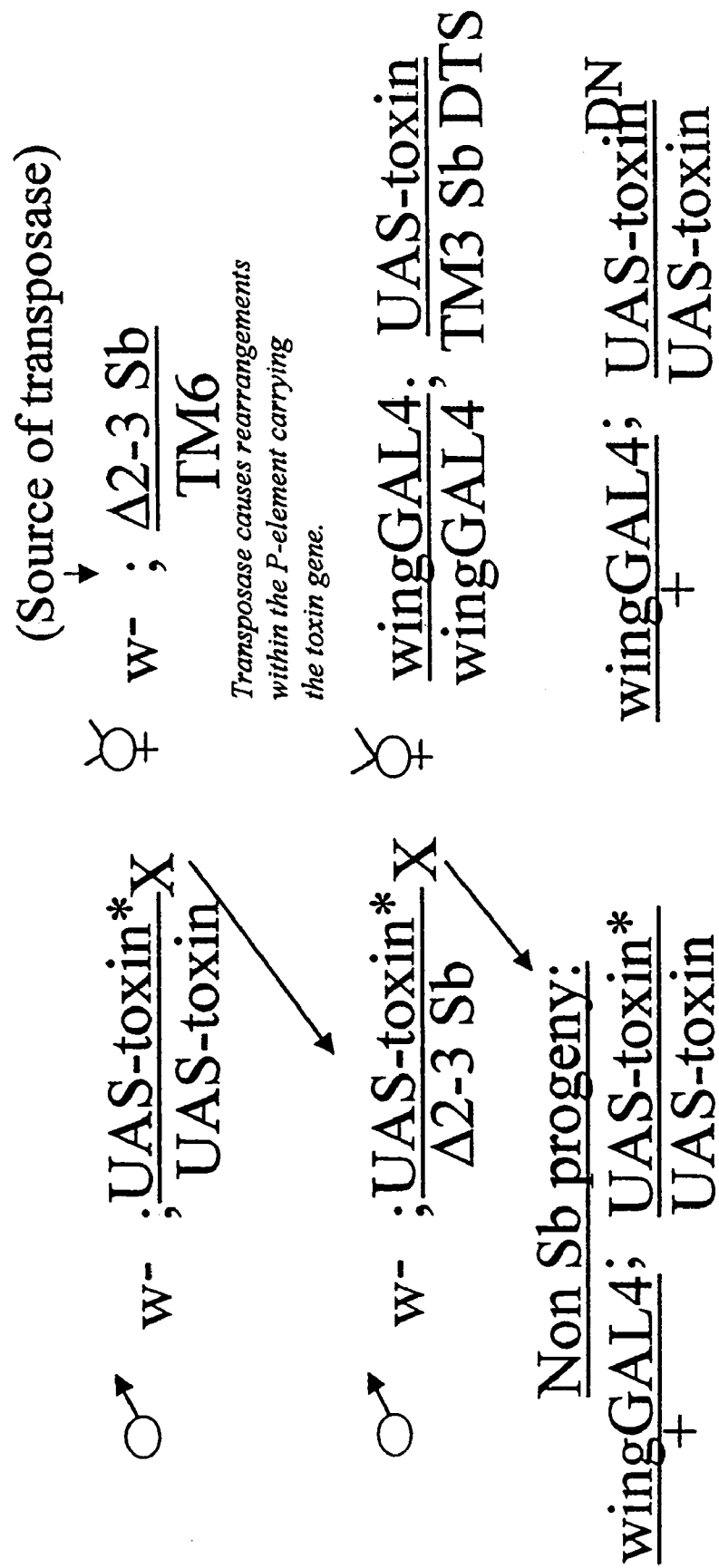

FIG. 13 is a basic scheme for creating Dominant-Negative alleles of bacterial toxins.

Figure 14:
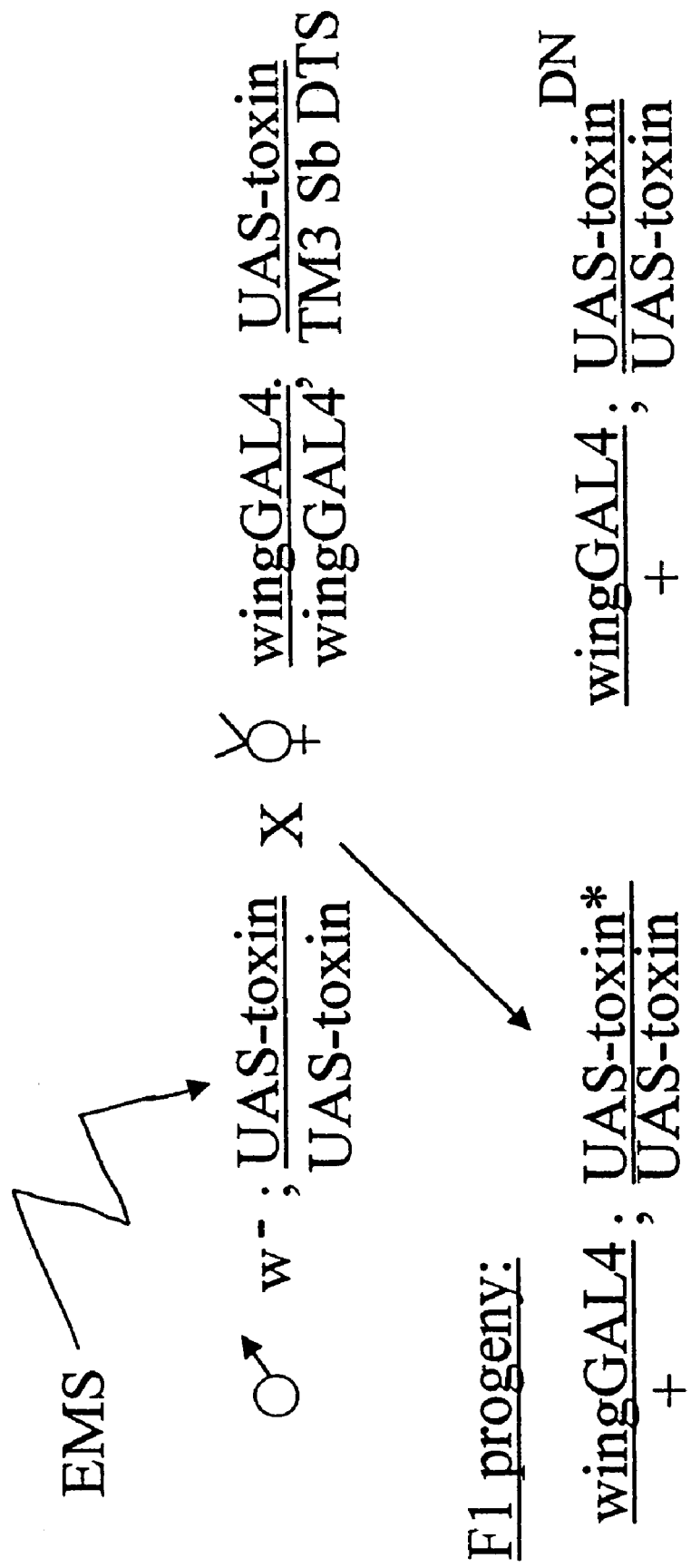

FIG. 14 is a variant genetic scheme using chemical mutagenesis

DESCRIPTION OF THE PREFERRED EMBODIMENTS

Introduction

Abbreviations: EGF-R, epidermal growth factor receptor; MAPK, mitogen-activated protein kinase; NOVA, novel overexpression activity; RNAi, RNA interference; UAS, upstream activation sequence; EMS, ethyl methanesulfonate.

The instant invention is a novel genetic method for generating a novel overexpression activity (hereinafter "NOVA") allele of a gene of interest (gene-x). Novel overexpression activity (NOVA) alleles of a gene of unknown function are powerful genetic tools that can provide important insights into the function of that gene. In addition, once a NOVA allele of a gene has been isolated, it is typically possible to design mutant screens to identify second site mutations in other genes acting in the same pathway as the gene of interest. Mutants in these second site modifier loci alter the NOVA phenotype, either by enhancing or suppressing that phenotype. Finally, it is possible to use mutagens to revert NOVA mutant phenotypes generated by this method and thereby efficiently generate second-site intragenic loss-of-function alleles within that gene of interest for structure/function studies.

The first step in this genetic method is to misexpress a wild-type (e.g. normal) copy of a gene in Drosophila and determine the phenotypic consequence of doing so. This type of analysis is routine using either heat inducible expression system (HS-gene-x) or the GAL4/UAS expression system (UAS-gene-x) of Brand and Perrimon (Brand and Perrimon, 1993). Once the phenotype due to misexpressing gene-x has been determined, which may not differ from wild-type, the novel idea is to:

1) Mutagenize flies carrying the gene-x transgene using chemical mutagens, radiation, or transposase induced mutagenesis.

2) Activate global or restricted expression (e.g. in time or space) of the mutagenized transgene (e.g. by heat inducing flies carrying a HS-gene-x transgene or by crossing flies carrying a UAS-gene-x transgene to one of the many available GAL4 drivers).

3) Screen for new dominant phenotypes resulting from expression of the mutagenized transgene-x such as constitutively active or dominant negative forms of the gene. Two examples of the use of this method are summarized below.

An important difference between this earlier screen and the NOVA mutagenesis described here is the use of a high-level expression system, which Inventors believe is critical for the recovery of novel activities that would otherwise go undetected.

The advantage of this method over existing methods is the efficiency and speed with which it can be applied to a wide variety of genes. Moreover, because our method is not predicated on assumptions based on protein domain structure and function, we can recover mutants in an unbiased fashion.

The Drosophila epidermal growth factor receptor (EGF-R) controls many critical cell-fate choices throughout development. Several proteins collaborate to promote localized EGF-R activation, such as Star and Rhomboid (Rho), which act sequentially to ensure the maturation and processing of inactive membrane-bound EGF ligands. To gain insights into the mechanisms underlying Rho and Star function, a mutagenesis scheme was developed to isolate novel overexpression activity (NOVA) alleles. In the case of rho, a dominant $^{Neo}$morphic allele was isolated, which interferes with Notch signaling, as well as a dominant-negative allele, which produces RNA interference-like flip-back transcripts that reduce endogenous rho expression. Also obtained were dominant-negative and $^{Neo}$morphic Star mutations, which have phenotypes similar to those of rho NOVA alleles, as well as dominant-negative Egf-r alleles.

Materials and Methods

Fly Stocks and Crosses.

Upstream activation sequence (UAS)-rho and pUAS-Star stocks were described in Guichard, A. et al (1999), the contents of which are incorporated herein. The pUAS-Egf-r and pUAS-Egf-r$^{DN1}$ stocks were provided by Allan Michelson (Brigham and Women's Hospital, Boston). All crosses were performed at 25° C.

Molecular Analysis of Mutations in rho, Star and Egf-r Transgenes.

For analysis of Δ2-3-induced mutants, sets of primers corresponding to sequences in the pUASt vector, the rho cDNA, or the Star cDNA were used to search for alterations in the various mutants by standard PCR or inverse PCR, with the Long Expand PCR system (Roche Molecular Biochemicals catalogue no. 1681842).

Immunoblot Analysis of Mutant Rho Proteins.

The anti-Rho serum (Sturtevant et al (1996)) was used for immunoblotting at 1/1,000 dilution, in 0.25% Tween 20, 1% milk in PBS. Secondary antibodies (horseradish peroxidase-coupled anti-rabbit IgG, Jackson ImmunoResearch catalogue no. 111-035-003) were used at 1/5,000 dilution. Chemiluminescent detection was performed by using the Supersignal kit (Pierce catalogue no. 34080).

In Situ Hybridization and Histochemistry.

In situ hybridization, histochemistry (O'Neill, J. & Bier, E. (1994)), and detection of MAPK activation (Guichard, A. et al (1999)), both references incorporated herein, were performed as described therein. Anti-Cut antibodies were obtained from the Developmental Studies Hybridoma Bank (University of Iowa).

Northern Analysis

Northern blots were prepared by using standard methods, hybridized with a horseradish peroxidase-labeled rho RNA probe, and detected by using the Chemiluminescent system CDP-Star (Amersham Pharmacia catalogue no. RPN3690).

General Genetic NOVA Screening Method

Male flies carrying a transgene-x are mutagenized, mated en masse to relevant female strains (see below for examples) and the progeny are then screened for novel NOVA phenotypes (e.g. phenotypes differing from that caused by misexpressing the wild-type transgene-x). The mutagen employed can be of any suitable type, including, but not limited to, chemical, X-ray

EXAMPLE 1

Mutagen=ethyl methane Sulfonate (EMS)
Transgene=HS-gene-x or p UAS-gene-x i. white-males carrying a white+ marked transgene-x on an autosomal chromosome denoted w−; p[w+gene-x]/p[w+gene-x] are crossed en masse to white-females (for HS-gene-x constructs) or white-; GAL4/GAL4 females (for UAS-gene-x constructs) at a ratio 25 mutagenized males to 50 females in bottles of fly food.

ii. Single progeny of this cross carrying a mutagenized transgene and the linked balancer chromosome denoted w−; p[w+gene-x*]; ÷GAL4 are then screened for a NOVA phenotype.

iii. Candidate NOVA mutants are then crossed to the appropriate balancer females to establish stable stocks, which are then retested for dependence on heat induction of GAL4 and analyzed further.

Figure 5F:
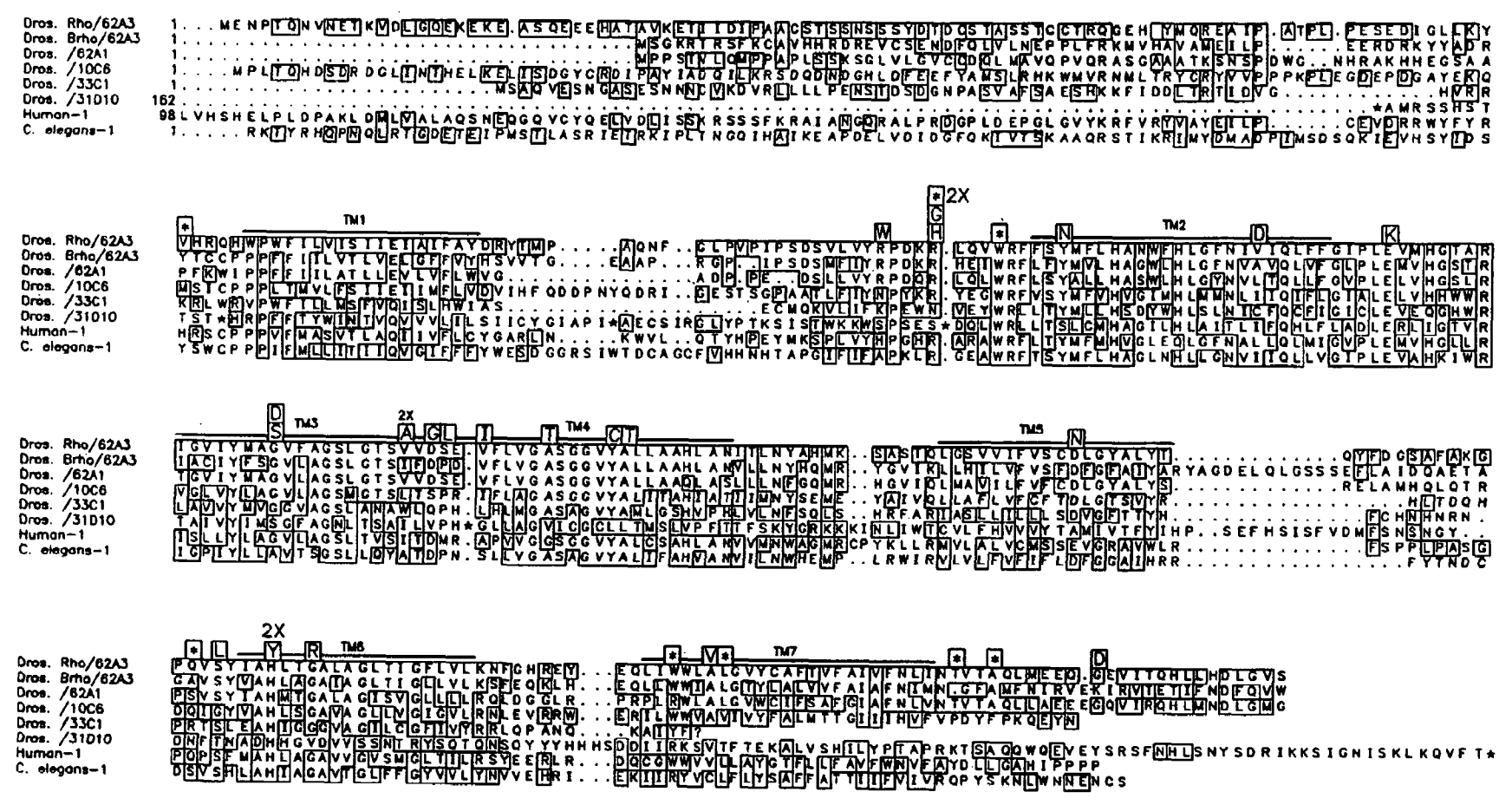

See FIG. 4 for an example of EMS induced mutations generated in a UAS-EGFR transgene to generate a dominant negative form of the EGF-Receptor. This method was also used (FIG. 5A) to generate loss-of-function rho alleles by mutagenizing flies carrying a constitutively active HS-rho construct that have ectopic veins as a consequence of the overexpression of the rho transgene (FIG. 5B) with EMS. Screening for revertants that have loss-of-function mutations in the rho transgene was performed (FIG. 5C-E). These rho revertant mutants have been sequenced to determine what regions of the Rho protein are critical for its ability to promote EGF-R signaling (FIG. 5F).

Advantage of EMS as a Mutagen

It is a relatively random mutagen that typically causes single amino acid substitutions.

Disadvantage of EMS as a Mutagen

It has no intrinsic bias for targeting the transgene versus all other endogenous genes for mutagenesis.

EXAMPLE 2

Mutagen=p-element Transposase enzyme
Transgene=pUAS-gene-x i. w−; p[w+UAS-gene-x]/p[w+UAS-gene-x] flies are crossed to flies carrying an activated form of transposase denoted w−; A2-3 Sb/TM6.

ii. Males of the genotype: w−; p[w+UAS-gene-x]; A2-3 Sb (transgene-x on the X-chromosome, second chromosome, or fourth chromosome) or w−; p[w+UAS-gene-x]/A2-35b (transgene-x on the third chromosome) are crossed to w−; GAL4/GAL4 females (the GAL4 driver of choice can be located on any chromosome) at a ratio of 3 mutagenized males to 8 females in vials of fly food (vials are used instead of bottles to insure that independent A2-3 induced mutations are recovered separately).

iii. Candidate NOVA mutants of the genotype w−; p[w+ UAS-gene-x]; GAL4 or w−; p[w+UAS-gene-x]/GAL4 are then crossed to the appropriate balancer females to establish stable stocks, which are then retested for GAL4 dependence and analyzed further.

Examples are shown of dominant NOVA and dominant negative phenotypes obtained from subjecting the UAS-sog (FIG. 2), UAS-EGFR (FIG. 4) and UAS-rho (FIG. 6) transgenes to A2-3 mutagenesis.

Advantage of Transposase as a Mutagen

Transposase induces a high frequency of mutations in transposable p-elements and thus in p-element based vectors containing transgenes (Daniels et al., 1985). This is a very efficient method for directing mutations to the transgene of interest.

Disadvantage of Transposase as a Mutagen

Transposase most frequently causes deletions and other large scale chromosomal aberrations rather than more restricted mutations such as amino acid substitutions.

Generation of Novel Mutations in Human Genes

The NOVA method can be used to generate novel mutations in human genes that can provide insight into the function of these genes and lead to the identification of medically relevant partners of these genes. This method is generally applicable because it can result in the efficient generation of activated and/or dominant negative NOVA-type mutations in a broad variety of genes. Since nearly all proteins interact with at least one other protein or substrate, it should be possible, in principle, to generate dominant negative alleles of virtually every gene if the mutant protein product interacts non-productively with such partners and is expressed at sufficiently high levels in the right place and time to titrate out those partners. Mutated transgenes can be sequenced to identify altered amino acid residues that are involved in potential protein-protein interactions. This information could then be used to design wild-type versus mutant peptides for yeast two hybrid screens to identify the putative protein partners that interact with the protein of interest. In contrast to this novel NOVA method, previously existing methods for generating dominant mutant phenotypes in model organisms such as *Drosophila* to study the function of a gene of interest are typically limited to the smaller subset of genes for which misexpression of the wild-type version of that gene generates a phenotype.

The NOVA method is expected to be applicable to other organisms including humans and model systems such as yeast, *C. elegans*, and *Arabidopsis*. Regarding potential applications to human disease, it should be possible to misexpress any of the over 1,000 currently identified human disease genes in *Drosophila*, and to use the NOVA method to isolate novel NOVA alleles of these genes. Once such a NOVA allele of a human disease gene has been isolated, it would be possible to perform second-site modifier screens to search for mutations in other genes, that when heterozygous, either enhance or suppress the human disease gene NOVA phenotype. This classic and effective use of *Drosophila* as a model genetic system for identifying all genes acting in a given pathway should reveal the identity of many *Drosophila* genes which interact with human disease genes. The majority of these *Drosophila* genes are expected to have human homologs that function equivalently, since over 50% of human disease genes have clear homologs in *Drosophila* (Reiter et al., 2000). Because the function of many of human disease genes and the partners with which they interact are typically unknown, Inventors anticipate that this NOVA genetic method will be a powerful tool for identifying and dissecting genetic pathways involved in human disease.

With respect to plants, isolation of NOVA alleles of plant genes controlling agriculturally relevant traits could lead to the development of new commercially valuable strains of plants. These NOVA alleles would also be valuable tools for conducting second-site modifier screens in *Arabidopsis*, analogous to those outlined above for *Drosophila*, to identify additional genes involved in controlling agriculturally desirable traits.

EXAMPLE 3

Isolation of rho Overexpression Alleles.

Rho has been recently defined as a novel type of intramembrane serine protease that cleaves the membrane-bound ligand Spi (mSpi) in the Golgi apparatus before its release into the extracellular space. Although a catalytic domain and key residues essential for proteolytic activity have been defined in Rho (Urban et al (2001)), it is not known which other parts of the protein fulfill regulatory functions and interact with functional partners such as Star or other components. Like many proteins recently identified in the *Drosophila* genome project, Rho does not contain any signature domains that could give clues about possible protein-protein interactions. In this context, Inventors developed a new strategy to screen for potential NOVA alleles of rho, which might provide additional insights into the mode of Rho action. The NOVA method makes use of the two-component GAL4/UAS expression system (Brand, A. H. & Perrimon, N. (1993)). The principle of this scheme is to expose a UAS transgene of interest to mutagenesis, express the mutated transgene in the $F_1$ progeny at high levels in a desired pattern by using a strong GAL4 driver, and then screen for novel visible phenotypes. In the present case, Inventors exposed a UAS-rho transgene to the $\Delta 2$-3 transposase, which induces rearrangements such as small deletions, inversions, and duplications within or adjacent to P element insertions as a byproduct of gap repair after excision events (Daniels et al (1985); Delattre et al (1995)). Inventors crossed individuals carrying the potentially mutagenized UAS-rho*transgene to flies carrying a strong ubiquitous wing-specific GAL4 driver (MS1096GAL4, referred to as wing-GAL4 hereafter) and then screened for novel dominant phenotypes in approximately 15,000 F1 progeny of this second cross (FIG. 7A). Among the individuals of the relevant wing-GAL4/UAS-rho* genotype, most flies exhibited the all-vein phenotype resulting from strong misexpression of unaltered wild-type UAS-rho (FIG. 7C). A smaller fraction of the F1 progeny had a wild-type phenotype, likely to reflect precise pUAS-rho excision events (FIG. 7B). In addition, Inventors recovered two individuals exhibiting distinct dominant NOVA phenotypes. The first mutant has small blistered wings with thickened veins and margin defects (FIG. 7D Inset). In the most-affected individuals, wings are virtually absent. Because loss-of-margin structures and great reduction in wing size are not phenotypes observed in loss-of-function rho mutants or in flies misexpressing wild-type rho, Inventors refer to this $^{Neo}$morphic rho mutant as rho$^{Neo}$. The second rho mutant had missing distal portions of wing veins (FIG. 7E) typical of rho loss-of-function situations (e.g., rhove, FIG. 7G). Inventors considered this NOVA mutant to be a likely dominant-negative form of rho (rho$^{DN}$).

EXAMPLE 4

Characterization of the Molecular Lesions in rhoNOVA Mutants.

As a first step in analyzing the new rho NOVA alleles, Inventors confirmed that the rho$^{Neo}$ and rho$^{DN}$ phenotypes were GAL4-dependent. Inventors then used combinations of PCR primer sets to amplify rho sequences within the pUAS vector and/or surrounding genomic sequences to identify molecular lesions responsible for the dominant rho$^{Neo}$ and rho$^{DN}$ activities. This analysis revealed that the UAS-rho$^{Neo}$ mutant carries a 5-kb deletion removing parts of both the rho cDNA and the adjacent white marker gene. This rho$^{Neo}$ mutant construct is predicted to encode a truncated protein containing the first 140 amino acids of Rho (including the N terminus, TM1, half of the first loop) and 10 amino acids encoded out-of-frame by the 3' end of the white gene, which are fused to the rho coding sequence (FIG. 7I, compare with wildtype structure in FIG. 7H).

Consistent with the predicted structure of Rho$^{Neo}$, immunoblotting of protein extracts from heat-induced HSGAL4>rho$^{Neo}$ flies by using an N-terminal specific anti-Rho antibody (Sturtevant et al (1996)) revealed high levels of a shorter-than-normal Rho protein (27 kDa instead of 43 kDa for the wild-type species; FIG. 7K, lanes 3 and 2, respectively). Interestingly, this Rho$^{Neo}$ protein comigrates with a smaller Rho protein species that is consistently observed on heat induction of full length Rho expression (FIG. 7K, lane 2).

Misexpression of components in the EGF-R pathway using the wing-GAL4 driver does not typically result in margin defects. It was therefore important to verify that the observed rho$^{Neo}$ phenotype resulted from misexpression of the truncated rho mutant transgene rather than from some adjacent genomic sequence. Although the pUASt vector does not activate expression of endogenous genes efficiently (Rørth et al (1998)), a general potential caveat to the NOVA method is that GAL4-dependent phenotypes could occasionally result from misexpression of an unrelated gene near the chromosomal site of a pUAS insertion. To address this concern, Inventors cloned a PCR product containing the truncated cDNA of the rho$^{Neo}$ gene back into the pUASt vector and retransformed this construct (named UAS-rho$^{Neo'}$) into flies. Misexpression of UAS-rho$^{Neo'}$ with the wing-GAL4 driver resulted in the same phenotype (FIG. 7F) as that obtained with the initial UAS-rho$^{Neo}$ isolate (FIG. 7D). Inventors conclude that the truncated rho$^{Neo}$ allele is indeed responsible for the observed wing phenotypes.

Molecular analysis of the UAS-rho$^{DN}$ mutation revealed an inverted duplication of the UAS and rho sequences with a spacer portion consisting of rho sequences (FIG. 7J). This UAS-rho$^{DN}$ mutant is predicted to generate an RNA with a hairpin structure (Guichard et al. PNAS), which potentially could exert an RNA interference (RNAi) effect (see below). Consistent with this prediction, a larger rho transcript ($\approx 3.9$ kb) observed in flies expressing rho$^{DN}$ (FIG. 7L, lane 3) than in those expressing wild-type rho (2.3 kb; FIG. 7L, lane 2).

EXAMPLE 5 rho$^{Neo}$ Interacts with the Notch Pathway.

Ubiquitous expression of rho$^{Neo}$ in the wing primordium disrupts formation of margin structures, suggesting that it interacts with a pathway involved in inducing margin cell fates or differentiation. To identify phenotypes specifically attributable to defects in wing margin cell fates, UAS-rho$^{Neo}$ with the margin-specific vestigial-GAL4 driver was expressed and a more pronounced loss of margin structures was observed (FIG. 8A) esembling that associated with reduction of wingless (wg) or Notch function (FIG. 8B). In addition, ubiquitous misexpression of UAS-rho$^{Neo}$ results in thickened veins (FIG. 7D)—another signature phenotype of Notch pathway mutants (FIG. 8B). Although ectopic or thickened veins can also result from misexpression of full-length rho (22,29), it is unlikely that rho$^{Neo}$ function is mediated by activation of EGF-R signaling or deregulated Rho protease activity, because this mutant lacks all sequences necessary for the proteolytic function of Rho (Lee et al (2001); Urban et al (2001)). It has also been reported that a dominant-negative form of EGF-R misexpressed in the margin causes notching (Nagaraj et al (1999)). However, because loss-of-function rho$^-$ or Egf-r$^-$ clones do not result in margin phenotypes (Diaz-Benjumea & Garcia-Bellido (1990); Diaz-Benjumea & Hafen (1994)), and because such loss-of-function mutations do not generate ectopic veins as observed in wing-GAL4/rho$^{Neo}$ wings, it seems unlikely that rho$^{DN}$ functions by a dominant-negative mechanism specific to the EGF-R pathway. The hypothesis that rho$^{Neo}$ interferes with Notch signaling was tested by assaying the expression of two downstream targets of Notch, wg and cut. In wild-type discs, wg and Cut are expressed in a narrow row of margin cells at the dorso-ventral boundary (FIGS. 8 E and G; Couso et al (1994) and Micchelli et al (1997)). In wing discs ubiquitously expressing the UAS-rho$^{Neo}$ construct, expression of both wg and Cut was abolished or significantly reduced (FIGS. 8 F and H), suggesting that rho$^{Neo}$ reduces Notch signaling. Consistent with this proposal, all rho$^{Neo}$ phenotypes are strongly suppressed by one copy of the activated N$^{Axl}$ allele in heterozygous females (FIG. 8D, compare with FIG. 7D). This N$^{Axl}$ allele, on its own, causes loss of veins when homozygous or hemizygous (FIG. 8C; Lindsley, D. & Zimm, G. (1992)), but has little effect when heterozygous.

One explanation for the rho$^{Neo}$ mutant phenotype is that it interferes with other Rho-related proteins (Wasserman et al (2000)). Consistent with this possibility, a human Rhomboid-like protein has been reported to bind the Notch-activating protease Presenilin (Pellegrini et al (2001)), suggesting a further connection between Rho-related proteins and Notch signaling. To determine whether Rho$^{Neo}$ interferes directly with the Notch pathway (e.g., by binding to a component of the Notch pathway and blocking its activity), or indirectly by impinging on other pathways interacting with Notch to promote margin development and vein formation, additional analysis will be required.

An important question regarding the biological significance of Rho$^{Neo}$ is whether a similar Rho fragment is generated in vivo and mediates a component of endogenous rho activity. It is relevant in this regard that an N-terminal Rho fragment of nearly identical size to rho$^{Neo}$ is consistently produced in vivo when full length Rho is overexpressed (FIG. 7K) and is also present in wild-type embryo extracts. One potential biological role for this N-terminal fragment of Rho could be the suppression of Notch activity in cells expressing high levels of Rho. Such negative feedback might aid in the creation of mutually exclusive domains of Notch and EGF-R activity in some developmental settings, as has been recently suggested for the partition of the eye disk into antenna and eye fields (Kumar & Moses (2001)) and for bristle differentiation (Culý' et al (2001)).

EXAMPLE 6 rho$^{DN}$ Inhibits EGF-R Activity by an RNAi-Like Mechanism.

To confirm that rho$^{DN}$ acts via a dominant-negative mechanism by inhibiting endogenous rho expression, and hence EGF-R activity, in situ activation of MAPK in wing discs expressing UAS-rho$^{DN}$ was examined. In the wing disk, MAPK activation revealed by an antibody specific for the diphosphorylated MAPK (Gabay et al (1997)), is restricted to vein and margin primordia and depends on localized rho expression and subsequent activation of EGF-R signaling (FIG. 9A; Guichard et al (1999); Gabay et al (1997) and Martý'n-Blanco et al (1999)). In line with rho expression defining the domain of EGF-R/MAPK signaling, ubiquitous activation of MAPK is observed in response to misexpression of UAS-rho (FIG. 9B; Guichard, A. et al (1999)). In contrast, overexpression of UAS-rho$^{DN}$ abolishes MAPK activation in, both, vein and margin primordia (FIG. 9C), consistent with rho$^{DN}$ inhibiting endogenous rho expression and subsequent EGF-R activation.

In support of rho$^{DN}$ functioning by an RNAi-like mechanism (Carthew (2001)), Rho protein could not be detected in extracts from the heat-induced UAS-rho$^{DN}$ flies (FIG. 7K, lane 4). In addition, UAS-rho$^{DN}$ transgene-derived RNA expression was nearly undetectable by in situ hybridization in wing-GAL4/UAS-rho$^{DN}$ wing imaginal discs (FIG. 9E), consistent with the formation of double-stranded RNA hairpin structures that are then degraded to 21- to 23-nt fragments, which would be inaccessible to hybridization. Critically, endogenous rho expression in vein and margin primordia (FIG. 9E Inset) was also absent in these discs, indicating that rho$^{DN}$ interferes with the expression or stability of the endogenous rho mRNA. A wild-type UAS-rho transgene was also coexpressed with UAS-rho$^{DN}$ and a significant overall reduction in the level of the wild-type rho mRNA (FIG. F, compare with D) and only a faint trace of Rho protein staining (FIG. 9H) relative to that produced by the wild-type UAS-rho transgene alone (FIG. 9G) was observed. The fact that Rho protein levels were more severely reduced than rho RNA levels in discs coexpressing rho and rho$^{DN}$ suggests that rho$^{DN}$ compromises translation of the wild-type rho RNA as well as reducing its stability. In line with these various observations, the all-vein phenotype of wings misexpressing wild-type UAS-rho (FIG. 9I) appeared almost completely suppressed by coexpression with UAS-rho$^{DN}$ (FIG. 9J). Cumulatively, these data indicate that rho$^{DN}$ acts by inhibiting the activity of rho, most likely by promoting the degradation of its RNA and blocking its translation. This example illustrates the potential utility of NOVA mutagenesis for creating an RNAi version of a gene of interest by purely genetic means, as an alternative to the time consuming and often problematic construction of RNAi inserts by in vitro engineering.

EXAMPLE 7

Isolation of NOVA Alleles of Star.

Because novel dominant rho alleles were readily generated by NOVA mutagenesis, Inventors wondered whether this scheme could be successfully applied to other UAS transgenes of interest. Because Star collaborates with rho and has no signature domain indicative of its function, it too is a good candidate for NOVA mutagenesis. Overexpression of wild-type Star typically results in no phenotype in the wing other than faint ectopic vein material near longitudinal veins (FIG. 10A). A UAS-Star transgene was submitted to the Δ2-3 transposase and the same wing-GAL4 driver was used to misexpress mutagenized Star insertions at high levels. In this screen of ≈15,000 progeny, Inventors recovered two types of GAL4-dependent dominant mutant alleles, referred to as Star$^{DN}$ and Star$^{Neo}$, which resulted in phenotypes nearly identical to those produced by misexpression of rho$^{DN}$ and rho$^{Neo}$. Thus, ubiquitous misexpression of Star$^{DN}$ results in vein truncation (FIGS. 10 B and C) similar to that observed in wings lacking Star activity (Guichard, A. et al (1999)), whereas misexpression of Star$^{Neo}$ alleles causes reduction in wing size, thickened veins, blisters, and strong disruption of margin structures (FIGS. 10 G and H). Consistent with Star$^{DN}$ acting in a dominant-negative fashion, coexpression of this mutant with wild-type Star suppresses the vein-loss phenotype of $Star^{DN}$ (FIG. 10D, compare with C). The nearly identical phenotypes produced by NOVA alleles of the rho and Star transgenes provide further evidence for the intimate functional relationship between rho and Star (Guichard, A. et al (1999)).

Molecular analysis of one $Star^{DN}$ mutation revealed that it is associated with an inversion, which has breakpoints mapping within the Star coding sequence and its 3' untranslated regions. As a result, the $Star^{DN}$ transgene is predicted to encode a shortened protein with a large C-terminal truncation preceding the single transmembrane domain of Star at amino acid 124 (FIG. 10J, compare with wild-type structure in I). Star is a predicted type II membrane protein with a cytoplasmic N terminus, suggesting that the $Star^{DN}$ peptide would be free in the cytoplasm. The C terminus of Star is required for binding to mSpi (Martý'n-Blanco et al (1999)) and promoting its transport from the endoplasmic reticulum to the Golgi (Lee et al (2001)). Because $Star^{DN}$ lacks the sequences necessary for interaction with mSpi, it is unlikely that it acts by titrating out Spitz-like ligands in an unproductive interaction. Consistent with this expectation, coexpression of $Star^{DN}$ with mSpi or mGrk did not restore a wild-type phenotype but rather resulted in increased vein-loss (FIG. 10F). It seems more likely, therefore, that the N-terminal region of Star normally interacts with another partner required for Spi maturation (e.g., Rho), and that the $Star^{DN}$ fragment binds and sequesters this partner in an inactive complex. In support of this view, coexpression of $Star^{DN}$ with rho efficiently suppresses rho-induced ectopic veins (FIG. 10E). Star may thus function in a multimeric complex that includes mSpi and Rho and/or some other component. According to this model, coexpression of $Star^{DN}$ with mSpi or mgrk would result in a greater titration of this endogenous factor and in an enhanced phenotype, as observed in FIG. 10F.

Inventors also analyzed the structures of two $Star^{Neo}$ mutants and found lesions mapping virtually to the same location. In both cases, a deletion fused C-terminal sequences of Star with the white marker. As a consequence, $Star^{Neo1}$ and $Star^{Neo2}$ encode Star proteins lacking 15 and 17 C-terminal amino acids, respectively, followed by different residues encoded by frameshift fusions to distinct white sequences (FIG. 10K). As in the case of the $rho^{Neo}$ mutant, overexpression of $Star^{Neo1}$ resulted in loss of wg and Cut expression in the margin primordia of third instar larval discs (data not shown). That $Star^{Neo2}$ is somewhat weaker than $Star^{Neo1}$ in inducing Notch-like phenotypes may result from the different C-terminal amino acids encoded by white sequences or may reflect a function of the two amino acids present in $Star^{Neo1}$ that are missing in $Star^{Neo2}$.

The strong similarity between $rho^{Neo}$ and $Star^{Neo}$ phenotypes suggests that they arise from interference with a common process. As a recent report shows that Star and Rho act sequentially rather than simultaneously (Lee et al (2001)), it is possible that the component(s) interacting with $rho^{Neo}$ and $Star^{Neo}$ act in the Golgi apparatus, where Star may hand over mSpi or other substrates to Rho for the final step of maturation.

EXAMPLE 8

Recovery of Distinct Classes of Dominant-Negative Egf-r Alleles in NOVA Screens.

The Egf-r gene is another good test case for NOVA analysis, because in vivo generated NOVA alleles could be compared with an existing dominant-negative Egf-r (Egf-$r^{DN1}$) construct created by in vitro genetic engineering (42). Strong ubiquitous expression of Egf-rwt in the wing results in moderate ectopic vein formation (FIG. 11A), whereas overexpression of Egf-$r^{DN1}$ results in small wings and vein loss (FIG. 11B). EGF-$R^{DN1}$ is a truncated version of the EGF-R lacking the cytoplasmic kinase domain (FIG. 11H, compare with Egf-rwt in G) and has been proposed to act primarily by forming nonfunctional heterodimers with endogenous wild-type EGF-R chains (Kashles et al (1991)). Inventors submitted the UAS-Egf-rwt transgene (FIG. 11G) to mutagenesis using either Δ2-3 transposase or ethyl methanesulfonate (EMS), and crossed the mutagenized males to wing-GAL4 females in two screens of 4,000 individuals each. New putative dominant-negative Egf-r alleles were recovered in both screens, which Inventors refer to as Egf $r^{DN2}$ and Egf-$r^{DN3}$, respectively. Misexpression of either of the pUAS-Eg-$r^{DN}$ alleles with the wing-GAL4 driver results in small curved wings and vein truncations (FIGS. 11 C and D), which are similar to, although somewhat weaker than, the phenotypes generated by misexpression of the reference Egfr$^{DN1}$ construct (FIG. 11B).

Molecular analysis of the Δ2-3 induced Egf-$r^{DN1}$ showed that this mutant is deleted for the entire kinase domain of the receptor and a small portion of the white marker, resulting in an "out-of-frame" fusion between the two genes, mapping 33 amino acids after the transmembrane domain of EGF-R (FIG. 11I). This structure is very similar to that of Egf-$r^{DN1}$, which has a STOP codon 20 amino acids after the transmembrane domain (FIG. 11H). The EMS-derived Egf-$r^{DN3}$ mutation results from a single amino acid substitution, R1062K, in the kinase domain of the receptor (FIG. 11J), consistent with the propensity of EMS to act as a point mutagen. This substitution is conservative; however, it alters a residue that is absolutely invariant among all tyrosine kinases and is immediately adjacent to the catalytic aspartate residue in the active site of the kinase domain (Johnson et al (1998)). Although Egf-$r^{DN2}$ and Egf-$r^{DN3}$ generate similar phenotypes in the wing, it was found that their activities differ when expressed with Egf-rwt Coexpression of Egf-$r^{DN2}$ (or Egf-$r^{DN1}$) with Egf-rwt results in mutual suppression of the Egf-rwt ectopic vein phenotype and of the Egf-$r^{DN2}$ vein-loss phenotype (FIG. 11E). In contrast, Egf-$r^{DN3}$ did not suppress the Egf-rwt phenotype, but instead interacted positively to produce smaller rounded wings with a strong all-vein phenotype (FIG. 11F). As the Egf-$r^{DN3}$ mutant retains a complete cytoplasmic domain that could interact with effector molecules, coexpression of this mutant with Egf-rwt may lead to the formation of EGF-$R^{DN3}$-EGF-$R^{wt}$ heterodimers with partial activity, as has been suggested for Egf-r alleles that exhibit interallelic complementation (Raz et al (1991)).

Perspectives on the General Utility of the NOVA Method.

An attractive feature of the NOVA mutagenesis scheme described above is that the transgene of interest is modified in vivo, without the need of in vitro genetic engineering followed by time-consuming transformation procedures. More critically, NOVA mutants are recovered in an unbiased fashion solely based on the nature of the phenotypes they induce. This phenotype-based screening eliminates the need for making predictions regarding likely functions of specific protein domains. Given that a substantial fraction of proteins predicted by genome sequencing have yet-unknown functions, the ability to screen for mutants without any advance knowledge of functional domains should be of significant utility. Although transposase is a particularly efficient mutagen for NOVA screening because it targets P element sequences, EMS can also be used in this scheme to create random point mutations. The different behaviors of the truncated Egf-$r^{DN2}$ and substitution Egf-$r^{DN3}$ mutants, when coexpressed with wild-type Egf-r, illustrate the value of screening for mutants with more than one type of mutagen. Point mutagens may also prove useful in creating NOVA mutations in endogenous genes adjacent to EP insertion lines (Rørth et al (1998)), which carry UAS sequences that can activate expression of neighboring genes in a GAL4-dependent fashion.

The ability of transposase to target rearrangements to sequences within P elements has been exploited previously to induce loss-of-function mutations in a hs-fused transgene (The'rond et al (1996)). An important difference between this earlier screen and the NOVA mutagenesis described here is the use of a high-level expression system, which Inventors believe is critical for the recovery of novel activities that would otherwise go undetected. For example, the two novel dominant-negative Egf-r alleles and the dominant-negative Star$^{DN}$ are very dosage sensitive. The requirement for high-level expression of dominant-negative constructs presumably reflects the need to produce a significant excess of the mutant protein relative to the endogenous protein to titrate out a sufficiently large fraction of the proteins or factors interacting with the wild-type protein. However, these high expression levels may also occasionally result in artifactual phenotypes caused by low-affinity interactions between proteins that would not ordinarily occur to a significant extent. It is therefore important to conduct additional experiments (e.g., with loss-of-function mutants, deficiencies, or duplications) to confirm the biological relevance of each NOVA phenotype.

The results disclosed hereinabove suggest that the NOVA method could be employed to generate dominant alleles of a wide range of genes using various mutagens and provide insight to the function and mechanism of action of novel genes. This approach should be of particular utility in investigating the function of human disease genes, which have no known functional motifs but have homologues in *Drosophila* (Reiter et al (2001)). Furthermore, NOVA mutagenesis should be applicable to any organism in which it is possible to misexpress transgenic constructs at high levels in a conditional fashion.

The abovementioned examples define a new method, the NOVA Method, that should be applicable to any system in which overexpression/misexpression is possible. The two specific examples that might be the most relevant are plants and single cell assays (e.g. frog oocytes or tissue culture cells). In the case of plants, the 35S misexpression system (patent held by Monsanto) or any tissue specific form of misexpression should make it possible to misexpress a given gene of interest either globally (35S) or in particular cell types (e.g. using enhancers specifically active in flowers, leaves, fruits, or roots). One could then perform NOVA exactly as described for *Drosophila* (e.g. mutagenize transgenic plants and screen for new dominant phenotypes genetically). Alternatively, since it is possible to transform plants at high efficiency using *Agrobacterium*, it should be possible to mutagenize a gene of interest in vitro using various PCR or targeted mutagenesis schemes, subclone the mutated pool of cDNAs into an expression vector (e.g. 35S), transform the mutated pool of cDNAs into plants, and then screen for dominant phenotypes.

In the case of frog oocytes one could mutate a gene of interest in vitro in an RNA expression vector, and inject pools of RNA made from these constructs into oocytes and look for a phenotype that differs from injection of the wild-type form of the gene. This could be a powerful way to conduct a structure function analysis of an ion channel gene. Similar in vitro mutagenesis schemes followed by transfection into cell culture lines could be designed for generating NOVA alleles of a gene and then assaying for phenotypes in cell culture (e.g. growth, DNA synthesis, DNA repair, altered cell morphology, altered expression of regulated luciferase expression etc.)

EXAMPLE 9

Method for Creating Dominant-Negative Forms of Bacterial Toxins

There is an existing need in combating intracellular bacterial toxins, especially now that we live in fear of terrorism. A viable approach to this problem is the creation of dominant-negative forms of bacterial toxins using NOVA screens in *Drosophila*.

Antibiotics and vaccines can prevent further bacterial growth, but do not inhibit the effect of already released bacterial toxins, which can destroy tissue without continued bacterial growth. Dominant-Negative versions of such toxins may in principle prevent their effects inside the infected cells. Over-expression of bacterial toxins in transgenic *Drosophila* lines could be used to reproduce the toxin-host cell interaction, and to screen for Dominant-Negative versions of these toxins. For example, FIG. 12 shows that many bacterial toxins modify Rho-like GTPases at specific residues, which are conserved in Rho/Rac fly homologues. This invention could be used to counter these toxin effects as follows:

1) The first step is to create transgenic flies able to express a bacterial toxin using the UAS/GAL4 conditional expression system. This is accomplished by preparing DNA encoding full-length bacterial toxin (e.g. from genomic clone, plasmid subclone, or by PCR), inserting the toxin-encoding gene into the pUAS-vector (Brand and Perrimon), transforming into *E. Coli* DH5α, testing for successful recombinants, preparing and purifying the pUAS-toxin DNA, injecting the w+ marked pUAS-toxin construct into w− fly embryos, isolating w+ transformants in F1 generation, establishing balanced transformed pUAS-toxin lines, expressing UAS-toxin in specific tissues using a set of GAL lines to generate viable phenotypes (e.g. wingless or eyeless phenotypes).

FIG. 13 is a basic scheme for creating Dominant-Negative alleles of bacterial toxins. In most cases, a very strong phenotype or death, is caused by two doses of wild-type toxin (e.g. wild-type toxin from female plus unmutated UAS-toxin* from male. In rare cases, a DN form of the toxin (toxin) reduces the phenotype caused by wild-type toxin.

FIG. 14 is a variant genetic scheme using chemical mutagenesis. In most cases, a very strong phenotype, or death, is caused by two doses of the wild-type toxin. In rare cases, the DN toxin counteracts the effect of the wild-type toxin: no or reduced phenotype.

2) The second step involves determining whether the *Drosophila* toxin phenotype is caused by the same mechanism as in human cells. This is done by analyzing the phenotype at the cellular level in third instar larvae. The procedure is as follows:

a. Analyze the phenotype at the cellular level in third instar larvae cytoskeleton (for toxins affecting Rho-like GTPases). Test the reorganization of the actin; determine the shape and size of the cells (for Cytolethal Distending Toxins); test the activity of MAPK using anti-diphosphoMAPK (for LF of *B. anthracis*); test the activity of Adenyl cyclase (for EF of *B. anthracis*); and test if the toxin induces cell-lethality, and whether it occurs through apoptosis or necrosis.

b. Use genetic epistatsis experiments to confirm that the cellular targets of the toxin are fly homologues of the human targets:

Test if the toxin-induced phenotype is modified in a heterozygous mutant background for the predicted target, and for their known partners; screen for enhancers of the toxin induced; and when the cellular target is not known, a phenotype analysis could be undertaken to identify such targets.

3) The third step is analyze the effect of the novel dominant-negative toxin. The procedure is to establish a mutant line carrying the UAS-toxinDN; determine what effect the toxinDN has when expressed alone (it should have no effect, even when expressed at high levels); determine by PCR what lesion has been created in the UAS-toxin insertion, and the corresponding altered protein sequence; clone a mutant toxinDN gene into a fresh pUAS vector; transform construct into flies; express in toxinDN gene flies with GAL4; and confirm that this is the only mutation required for DN toxin activity.

While the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

REFERENCES

Bang, A. G. & Kintner, C. (2000) *Genes Dev.* 14, 177-186.
Bier, E. (1998) *BioEssays* 20, 189-194.
Bier, E., Jan, L. Y. & Jan, Y. N. (1990) *Genes Dev.* 4, 190-203.
Brand, A. H. & Pernimon, N. (1993) Development (Cambridge, UK) 118, 401-415.
Brand, A. H., and Pernimon, N. (1993). Development 118, 401-415.
Buff, E., Carmena, A., Gisselbrecht, S., Jimenez, F. & Michelson, A. (1998) Development (Cambridge, UK) 125, 2075-2086.
Carthew, R (2001) Curr. Opin. Cell Biol. 13, 244-248.
Couso, J., Bishop, S. & Martinez Arias, A. (1994) Dev. Biol. 120, 621-636.
Culý', J., Martý'n-Blanco, E. & Modolell, J. (2001) Development (Cambridge, UK) 128, 299-308.
Daniels S. B., McCarron, M., Love, C, Chovnick, A. (1985). Genetics 109, 95-117.
Daniels, S., McCarron, M., Love, C. & Chovnick, A. (1985) Genetics 109, 95-117.
Delattre, M., Anxolabe'he're, D. & Coen, D. (1995) Genetics 141, 1407-1424.
Diaz-Benjumea, F. J. & Garcia-Bellido, A. (1990) Proc. R. Soc. London Ser. B. 242, 36-44.
Diaz-Benjumea, F. J. & Hafen, E. (1994) Development (Cambridge, UK) 120, 569-578.
Ferguson, E. L. and K. V. Anderson. (1992). Development 114, 583-597.
François, V., M. Solloway, J. W. O'Neill, J. Emery, and E. Bier. (1994). Genes and Dev. 8, 2602-2616.
Gabay, L., Seger, R. & Shilo, B. Z. (1997) Development (Cambridge, UK) 124, 3535-3541.
Gabay, L., Seger, R. & Shilo, B.-Z. (1997) Science 277, 1103-1106.
Golembo, M., Raz, E. & Shilo, B.-Z. (1996) Development (Cambridge, UK) 122, 3363-3370.
Guichard et al. PNAS_Mar. 19, 2002_vol. 99_no. 6_3757.
Guichard, A., Biehs, B., Sturtevant, M., Wickline, L., Chacko, J., Howard, K. & Bier, E. (1999) Development (Cambridge, UK) 126, 2663-2676.
Guichard, A., Roark, M, Ronshaugen, M. & Bier, E. (2000) Dev. Biol. 226, 255-266.
Hsiung, F., Griffis, E., Pickup, A., Powers, M. & Moses, K. (2001) Mech. Dev. 107, 13-23.
Johnson, L. N., Lowe, E. D., Noble, M. E. & Owen, D. J. (1998) FEBS Lett. 430, 1-11.

Kashles, O., Yarden, Y., Fischer, R, Ulrich, A. & Schlessinger, J. (1991) Mol. Cell. Biol. 11, 1454-1463.
Kolodkin, A. L., Pickup, A. T., Lin, D. M., Goodman, C. S. & Banerjee, U. (1994) Development (Cambridge, UK) 120, 1731-1745.
Kumar, J. & Moses, K. (2001) Cell 104, 687-697.
Lee, J. R., Urban, S., Garvey, C. F. & Freeman, M. (2001) Cell 107, 161-171.
Lindsley, D. & Zimm, G. (1992) The Genome of *Drosophila melanogaster* (Academic, New York).
Martý'n-Blanco, E., Roch, F., Noll, E., Baonza, A., Duffy, J. & Perrimon, N. (1999) Development (Cambridge, UK) 126, 5739-5747.
Micchelli, C, Rulifson, E. & Blair, S. (1997) Dev. Biol. 124, 1485-1495.
Moghal, N. & Sternberg, P. (1999) Curr. Opin. Cell Biol. 11, 190-196.
Nagaraj, R., Pickup, A., Howes, R., Moses, K., Freeman, M. & Banerjee, U. (1999) Development (Cambridge, UK) 126, 975-985.
Neuman-Silberberg, F. S. & Schu'pbach, T. (1993) Cell 75, 165-174.
Noll, R., Sturtevant, M. A., Gollapudi, R. R. & Bier, E. (1994) Development (Cambridge, UK) 120, 2329-2338.
O'Neill, J. & Bier, E. (1994) BioTechniques 17, 870-874.
Pellegrini, L., Passer, B. J., Canelles, M., Lefterov, I., Ganjei, J. K., Fowlkes, B. J., Koonin, E. V. & D'Adamio, L. (2001) J. Alz. Dis. 3, 181-190.
Penimon, N. & Perkins, L. A. (1997) Cell 89, 13-16.
Pickup, A. & Banerjee, U. (1999) Dev. Biol. 205, 254-259.
Raz, E., Schejter, E. D. & Shilo, B. Z. (1991) Genetics 129, 191-201.
Reiter, L. T., Potocki, L., Chien, S., Gribskov, M. & Bier, E. (2001) Gen. Res. 11, 1114-1125.
Reiter, L., E. Bier, and M. Gribskov. (2000). Homophila, (http://homophila.sdsc.edu) UCSD.
Rørth, P., Szabo, K., Bailey, A., Layerty, T., Rehm, J., Rubin, G., Weigmarm, K., Mila'n, M, Benes, V., Ansorge, W. & Cohen, S. (1998) Dev. Biol. 125, 1049-1057.
Rutledge, B. J., Zhang, K., Bier, E., Jan, Y. N. & Perrimon, N. (1992) Genes Dev. 6, 1503-1517.
Schnepp, B., Grumbling, G, Donaldson, T. & Simcox, A. (1996) Genes Dev. 10, 2302-2313.
Schweitzer, R. & Shilo, B. Z. (1997) Trends Genet. 13, 191-196.
Schweitzer, R., Shaharabany, M., Seger, R & Shilo, B.-Z. (1995) Genes Dev. 9, 1518-1529.
Sturtevant, M. A., Roark, M. & Bier, E. (1993) Genes Dev. 7, 961-973.
Sturtevant, M. A., Roark, M., O'Neill, J. W., Biehs, B., Colley, N. & Bier, E. (1996) Dev. Biol. 174, 298-309.
The'rond, P., Alves, G., Limbourg-Bouchon, B., Tricoire, H., Guillemet, E., Brissard-Zahraoui, J., Lamour-Isnard, C. & Busson, D. (1996) Genetics 142, 1181-1198.
Tsruya, R., Schlesinger, A., Reich, A., Gabay, L., Sapir, A. & Shilo, B. Z. (2002) Genes Dev. 16, 222-234.
Urban, S., Lee, J. R. & Freeman, M. (2001) Cell 107, 173-182.
Wasserman, J. D., Urban, S. & Freeman, M. (2000) Genes Dev. 14, 1651-1663.
Wieschaus, E., C. Nüsslein-Volhard, and G. Jürgens. (1984). Roux's Arch. Dev. Biol. 193, 296-307.
Yu, K., M. A. Sturtevant, B. Biehs, V. Francois, R Padgett, R. Blackman, and E. Bier. (1996). Development 122, 4033-4044.
Yu, K., S. Srinivasan, O. Shimmi, B. Biehs, K. E. Rashka, D. Kimelman, M. B. O'Connor, and E. Bier. (2000). Development 127, 2143-2154.

What is claimed is:

1. A method for generating dominant-negative forms of bacterial toxins, comprising the steps of:
   a. misexpressing a wild-type bacterial toxin gene of interest in *Drosophila* flies, using a GAL4/UAS expression system;
   b. determining the phenotypic consequence of such misexpression, and selecting flies in which the bacterial toxin gene of interest is expressed;
   c. mutagenizing the wild-type bacterial toxin gene in the selected flies to produce carriers of a mutant bacterial toxinDN gene that differs in structure from the wild-type toxin gene by
      i. preparing DNA encoding full-length bacterial toxin,
      ii. inserting the toxin-encoding gene into the pUAS-vector
      iii. transforming into *E. coli* DH5ÿ,
      iv. testing for successful recombinants,
      v. purifying the pUAS-toxin DNA,
      vi. injecting the pUAS-toxin construct comprising a marked transgene into fly embryos without the marked transgene, isolating transformants comprising the marked transgene in F1 generation carrying a mutant bacterial toxinDN, and
      vii. selecting and establishing balanced transformed pUAS-toxinDN fly lines; and
   d. causing the mutant bacterial toxin gene to be expressed in the selected flies by expressing UAS-toxin in specific tissues using a set of GAL lines.

2. The method according to claim 1, further comprising analyzing the activity of the novel dominant-negative toxin by
   a. establishing a mutant line carrying the UAS-toxinDN,
   b. determining what effect the toxinDN has when expressed alone,
   c. determining by PCR if a lesion has been created in the UAS-toxin insertion and the corresponding altered protein sequence,
   d. cloning a mutant toxinDN gene into a fresh pUAS vector to obtain a construct,
   e. transforming the construct into flies,
   f. expressing in toxinDN gene flies with GAL4; and
   g. confirming that the mutation is the only mutation required for the toxinDN activity.

3. The method according to claim 2, wherein the mutations involve lethal factor (LF) of *B. anthracis*, the method further comprising analyzing the activity of MAPK using anti-diphosphoMAPK antibody.

4. The method according to claim 2, wherein the mutations involve LF of *B. anthracis*, the method further comprising analyzing the activity of Adenyl cyclase in the presence of the toxinDN.

5. The method according to claim 2, wherein the mutations involve Cytolethal Distending Toxins, the method further comprising observing the reorganization of actin to determine the shape and size of the cells developed in the presence of the toxinDN.

6. The method according to claim 1, further comprising a step d' of determining whether the *Drosophila* toxin phenotype is caused by the same mechanism as in human cells by:
   d'. analyzing the phenotype at the cellular level in third instar larvae cytoskeleton for toxins affecting Rho-like GTPases by testing if the toxin induces cell-lethality and whether it occurs through apoptosis or necrosis.

7. The method according to claim 6, wherein the step d' of determining whether the *Drosophila* toxin phenotype is caused by the same mechanism as in human cells is accomplished with genetic epistatsis experiments.

8. The method according to claim 7, wherein the genetic epistatsis experiments performed in step d' include the steps of:
   i. testing to determine if the toxin-induced phenotype is modified in a heterozygous mutant background for the predicted target and for their known partners,
   ii. screening for enhancers of the toxin induced, and
   iii. performing a phenotype analysis to identify such targets when the cellular target is not known.

* * * * *

SEQUENCE LISTING

<160> NUMBER OF SEQ ID NOS: 27

<210> SEQ ID NO 1
<211> LENGTH: 29
<212> TYPE: PRT
<213> ORGANISM: Drosophila sp.

<400> SEQUENCE: 1

Ser Glu Pro Leu Arg Pro Ser Gly Val Arg Thr Ala Thr His Lys Asn
 1               5                  10                  15

Pro Lys Pro Gln Met Val Thr Arg Asn Arg Leu Phe Trp
            20                  25

<210> SEQ ID NO 2
<211> LENGTH: 354
<212> TYPE: PRT
<213> ORGANISM: Drosophila sp.

<400> SEQUENCE: 2

Met Glu Asn Pro Thr Gln Asn Val Asn Glu Thr Lys Val Asp Leu Gly
 1               5                  10                  15

Gln Glu Lys Glu Lys Glu Ala Ser Gln Glu Glu His Ala Thr Ala
            20                  25                  30

Val Lys Glu Thr Ile Ile Asp Ile Pro Ala Ala Cys Ser Thr Ser Ser
         35                  40                  45

Asn Ser Ser Ser Tyr Asp Thr Asp Cys Ser Thr Ala Ser Ser Thr Cys
     50                  55                  60

Cys Thr Arg Gln Gly Glu His Tyr Met Gln Arg Glu Ala Ile Pro Ala
 65                  70                  75                  80

Thr Pro Leu Pro Glu Ser Glu Asp Ile Gly Leu Leu Lys Tyr Val His
                 85                  90                  95

Arg Gln His Trp Pro Trp Phe Ile Leu Val Ile Ser Ile Ile Glu Ile
            100                 105                 110

Ala Ile Phe Ala Tyr Asp Arg Tyr Thr Met Pro Ala Gln Asn Phe Gly
        115                 120                 125

Leu Pro Val Pro Ile Pro Ser Asp Ser Val Leu Val Tyr Arg Pro Asp
    130                 135                 140

Arg Arg Leu Gln Val Trp Arg Phe Ser Tyr Met Phe Leu His Ala
145                 150                 155                 160

Asn Trp Phe His Leu Gly Phe Asn Ile Val Ile Gln Leu Phe Phe Gly
                165                 170                 175

Ile Pro Leu Glu Val Met His Gly Thr Ala Arg Ile Gly Val Ile Tyr
            180                 185                 190

Met Ala Gly Val Phe Ala Gly Ser Leu Gly Thr Ser Val Val Asp Ser
        195                 200                 205

Glu Val Phe Leu Val Gly Ala Ser Gly Val Tyr Ala Leu Leu Ala
    210                 215                 220

Ala His Leu Ala Asn Ile Thr Leu Asn Tyr Ala His Met Lys Ser Ala
225                 230                 235                 240

Ser Thr Gln Leu Gly Ser Val Val Ile Phe Val Ser Cys Asp Leu Gly
                245                 250                 255

Tyr Ala Leu Tyr Thr Gln Tyr Phe Asp Gly Ser Ala Phe Ala Lys Gly
            260                 265                 270

Pro Gln Val Ser Tyr Ile Ala His Leu Thr Gly Ala Leu Ala Gly Leu
        275                 280                 285

```
Thr Ile Gly Phe Leu Val Leu Lys Asn Phe Gly His Arg Glu Tyr Glu
    290                 295                 300

Gln Leu Ile Trp Trp Leu Ala Leu Gly Val Tyr Cys Ala Phe Thr Val
305                 310                 315                 320

Phe Ala Ile Val Phe Asn Leu Ile Asn Thr Val Thr Ala Gln Leu Met
                325                 330                 335

Glu Glu Gln Gly Glu Val Ile Thr Gln His Leu Leu His Asp Leu Gly
                340                 345                 350

Val Ser

<210> SEQ ID NO 3
<211> LENGTH: 331
<212> TYPE: PRT
<213> ORGANISM: Drosophila sp.

<400> SEQUENCE: 3

Met Ser Gly Lys Arg Thr Arg Ser Phe Lys Cys Ala Val His His Arg
  1               5                  10                  15

Asp Arg Glu Val Cys Ser Glu Asn Asp Phe Gln Leu Val Leu Asn Glu
             20                  25                  30

Pro Pro Leu Phe Arg Lys Met Val His Ala Val Ala Met Glu Ile Leu
         35                  40                  45

Pro Glu Glu Arg Asp Arg Lys Tyr Tyr Ala Asp Arg Tyr Thr Cys Cys
 50                  55                  60

Pro Pro Pro Phe Phe Ile Ile Leu Val Thr Leu Val Glu Leu Gly Phe
 65                  70                  75                  80

Phe Val Tyr His Ser Val Val Thr Gly Glu Ala Ala Pro Arg Gly Pro
                 85                  90                  95

Ile Pro Ser Asp Ser Met Phe Ile Tyr Arg Pro Asp Lys Arg His Glu
            100                 105                 110

Ile Trp Arg Phe Leu Phe Tyr Met Val Leu His Ala Gly Trp Leu His
        115                 120                 125

Leu Gly Phe Asn Val Ala Val Gln Leu Val Phe Gly Leu Pro Leu Glu
130                 135                 140

Met Val His Gly Ser Thr Arg Ile Ala Cys Ile Tyr Phe Ser Gly Val
145                 150                 155                 160

Leu Ala Gly Ser Leu Gly Thr Ser Ile Phe Asp Pro Asp Val Phe Leu
                165                 170                 175

Val Gly Ala Ser Gly Gly Val Tyr Ala Leu Leu Ala Ala His Leu Ala
            180                 185                 190

Asn Val Leu Leu Asn Tyr His Gln Met Arg Tyr Gly Val Ile Lys Leu
        195                 200                 205

Leu His Ile Leu Val Phe Val Ser Phe Asp Phe Gly Phe Ala Ile Tyr
210                 215                 220

Ala Arg Tyr Ala Gly Asp Glu Leu Gln Leu Gly Ser Ser Ser Glu Phe
225                 230                 235                 240

Leu Ala Ile Asp Gln Ala Glu Thr Ala Gly Ala Val Ser Tyr Val Ala
                245                 250                 255

His Leu Ala Gly Ala Ile Ala Gly Leu Thr Ile Gly Leu Leu Val Leu
            260                 265                 270

Lys Ser Phe Glu Gln Lys Leu His Glu Gln Leu Leu Trp Trp Ile Ala
        275                 280                 285

Leu Gly Thr Tyr Leu Ala Leu Val Val Phe Ala Ile Ala Phe Asn Ile
290                 295                 300
```

```
Met Asn Gly Phe Ala Met Phe Asn Ile Arg Val Glu Lys Ile Arg Val
305                 310                 315                 320

Thr Glu Thr Ile Phe Asn Asp Phe Gln Val Trp
            325                 330

<210> SEQ ID NO 4
<211> LENGTH: 314
<212> TYPE: PRT
<213> ORGANISM: Drosophila sp.

<400> SEQUENCE: 4

Met Pro Pro Ser Thr Val Leu Gln Met Pro Ala Pro Leu Ser Ser
 1               5                  10                  15

Lys Ser Gly Leu Val Leu Gly Val Cys Cys Asp Gln Leu Met Ala Val
                20                  25                  30

Gln Pro Val Gln Arg Ala Ser Gly Ala Ala Thr Lys Ser Asn Ser
             35                  40                  45

Pro Asp Trp Gly Asn His Arg Ala Lys His Glu Gly Ser Ala Ala
     50                  55                  60

Pro Phe Lys Trp Ile Pro Pro Phe Phe Ile Ile Leu Ala Thr Leu Leu
 65                  70                  75                  80

Glu Val Leu Val Phe Leu Trp Val Gly Ala Asp Pro Pro Glu Asp Ser
                 85                  90                  95

Leu Leu Val Tyr Arg Pro Asp Gln Arg Leu Gln Leu Trp Arg Phe Leu
                100                 105                 110

Ser Tyr Ala Leu Leu His Ala Ser Trp Leu His Leu Gly Tyr Asn Val
                115                 120                 125

Leu Thr Gln Leu Leu Phe Gly Val Pro Leu Glu Leu Val His Gly Ser
    130                 135                 140

Leu Arg Thr Gly Val Ile Tyr Met Ala Gly Val Leu Ala Gly Ser Leu
145                 150                 155                 160

Gly Thr Ser Val Val Asp Ser Glu Val Phe Leu Val Gly Ala Ser Gly
                165                 170                 175

Gly Val Tyr Ala Leu Leu Ala Ala Gln Leu Ala Ser Leu Leu Leu Asn
                180                 185                 190

Phe Gly Gln Met Arg His Gly Val Ile Gln Leu Met Ala Val Ile Leu
                195                 200                 205

Phe Val Phe Cys Asp Leu Gly Tyr Ala Leu Tyr Ser Arg Glu Leu Ala
    210                 215                 220

Met His Gln Leu Gln Thr Arg Pro Ser Val Ser Tyr Ile Ala His Met
225                 230                 235                 240

Thr Gly Ala Leu Ala Gly Ile Ser Val Gly Leu Leu Leu Arg Gln
                245                 250                 255

Leu Asp Gly Gly Leu Arg Pro Arg Pro Leu Arg Trp Leu Ala Leu Gly
            260                 265                 270

Val Trp Cys Ile Phe Ser Ala Phe Gly Ile Ala Phe Asn Leu Val Asn
    275                 280                 285

Thr Val Thr Ala Gln Leu Leu Ala Glu Glu Gly Gln Val Ile Arg
                290                 295                 300

Gln His Leu Met Asn Asp Leu Gly Met Gly
305                 310

<210> SEQ ID NO 5
<211> LENGTH: 342
<212> TYPE: PRT
<213> ORGANISM: Drosophila sp.
```

<400> SEQUENCE: 5

```
Met Pro Leu Thr Gln His Asp Ser Asp Arg Asp Gly Leu Ile Asn Thr
 1               5                  10                  15

His Glu Leu Lys Glu Leu Ile Ser Asp Gly Tyr Cys Arg Asp Ile Pro
             20                  25                  30

Ala Tyr Ile Ala Asp Gln Ile Leu Lys Arg Ser Asp Gln Asp Asn Asp
         35                  40                  45

Gly His Leu Asp Phe Glu Glu Phe Tyr Ala Met Ser Leu Arg His Lys
     50                  55                  60

Trp Met Val Arg Asn Met Leu Thr Arg Tyr Cys Arg Tyr Val Val Pro
 65                  70                  75                  80

Pro Pro Lys Pro Leu Glu Gly Asp Glu Pro Asp Gly Ala Tyr Glu Lys
                 85                  90                  95

Gln Met Ser Ile Cys Pro Pro Leu Thr Met Val Leu Phe Ser Ile
            100                 105                 110

Ile Glu Ile Ile Met Phe Leu Val Asp Val Ile His Phe Gln Asp Asp
            115                 120                 125

Pro Asn Tyr Gln Asp Arg Ile Gly Glu Ser Thr Ser Gly Pro Ala Ala
130                 135                 140

Thr Leu Phe Ile Tyr Asn Pro Tyr Lys Arg Tyr Glu Gly Trp Arg Phe
145                 150                 155                 160

Val Ser Tyr Met Phe Val His Val Gly Ile Met His Leu Met Met Asn
                165                 170                 175

Leu Ile Ile Gln Ile Phe Leu Gly Ile Ala Leu Glu Leu Val His His
            180                 185                 190

Trp Trp Arg Val Gly Leu Val Tyr Leu Ala Gly Val Leu Ala Gly Ser
            195                 200                 205

Met Gly Thr Ser Leu Thr Ser Pro Arg Ile Phe Leu Ala Gly Ala Ser
        210                 215                 220

Gly Gly Val Tyr Ala Leu Ile Thr Ala His Ile Ala Thr Ile Ile Met
225                 230                 235                 240

Asn Tyr Ser Glu Met Glu Tyr Ala Ile Val Gln Leu Leu Ala Phe Leu
                245                 250                 255

Val Phe Cys Phe Thr Asp Leu Gly Thr Ser Val Tyr Arg His Leu Thr
            260                 265                 270

Asp Gln His Asp Gln Ile Gly Tyr Val Ala His Leu Ser Gly Ala Val
            275                 280                 285

Ala Gly Leu Leu Val Gly Ile Gly Val Leu Arg Asn Leu Glu Val Arg
        290                 295                 300

Arg Trp Glu Arg Ile Leu Trp Trp Val Ala Val Ile Val Tyr Phe Ala
305                 310                 315                 320

Leu Met Thr Thr Gly Ile Ile Ile His Val Phe Val Pro Asp Tyr Phe
                325                 330                 335

Pro Lys Gln Glu Tyr Asn
            340
```

<210> SEQ ID NO 6
<211> LENGTH: 264
<212> TYPE: PRT
<213> ORGANISM: Drosophila sp.
<220> FEATURE:
<221> NAME/KEY: UNSURE
<222> LOCATION: (264)
<223> OTHER INFORMATION: Variable amino acid may or may not be present

<400> SEQUENCE: 6

```
Met Ser Ala Gln Val Glu Ser Asn Gly Ala Ser Glu Ser Asn Asn Asn
 1               5                  10                  15

Cys Val Lys Asp Val Arg Leu Leu Leu Pro Glu Asn Ser Thr Asp
             20                  25                  30

Ser Asp Gly Asn Pro Ala Ser Val Ala Phe Ser Ala Glu Ser His Lys
         35                  40                  45

Lys Phe Ile Asp Asp Leu Thr Arg Thr Ile Asp Val Gly His Val Arg
     50                  55                  60

Arg Lys Arg Leu Trp Arg Val Pro Trp Phe Ile Leu Leu Met Ser Phe
 65                  70                  75                  80

Val Gln Ile Ser Leu His Trp Ile Ala Ser Glu Cys Met Gln Lys Val
                 85                  90                  95

Leu Ile Phe Lys Pro Glu Trp Asn Val Glu Tyr Trp Arg Leu Leu Thr
            100                 105                 110

Tyr Met Leu Leu His Ser Asp Tyr Trp His Leu Ser Leu Asn Ile Cys
        115                 120                 125

Phe Gln Cys Phe Ile Gly Ile Cys Leu Glu Val Glu Gln Gly His Trp
    130                 135                 140

Arg Leu Ala Val Val Tyr Met Val Gly Gly Val Ala Gly Ser Leu Ala
145                 150                 155                 160

Asn Ala Trp Leu Gln Pro His Leu His Leu Met Gly Ala Ser Ala Gly
                165                 170                 175

Val Tyr Ala Met Leu Gly Ser His Val Pro His Leu Val Leu Asn Phe
            180                 185                 190

Ser Gln Leu Ser His Arg Phe Ala Arg Ile Ala Ser Leu Leu Ile Leu
        195                 200                 205

Leu Leu Ser Asp Val Gly Phe Thr Thr Tyr His Phe Cys His Asn His
    210                 215                 220

Asn Arg Asn Pro Arg Thr Ser Leu Glu Ala His Ile Gly Gly Gly Val
225                 230                 235                 240

Ala Gly Ile Leu Cys Gly Phe Ile Val Tyr Arg Arg Leu Gln Pro Ala
                245                 250                 255

Asn Gln Lys Ala Ile Tyr Phe Xaa
            260
```

<210> SEQ ID NO 7
<211> LENGTH: 11
<212> TYPE: PRT
<213> ORGANISM: Drosophila sp.

<400> SEQUENCE: 7

```
Ala Met Arg Ser Ser His Ser Thr Thr Ser Thr
 1               5                  10
```

<210> SEQ ID NO 8
<211> LENGTH: 29
<212> TYPE: PRT
<213> ORGANISM: Drosophila sp.

<400> SEQUENCE: 8

```
His Arg Pro Phe Phe Thr Tyr Trp Ile Asn Thr Val Gln Val Val Val
 1               5                  10                  15

Leu Ile Leu Ser Ile Ile Cys Tyr Gly Ile Ala Pro Ile
             20                  25
```

```
<210> SEQ ID NO 9
<211> LENGTH: 25
<212> TYPE: PRT
<213> ORGANISM: Drosophila sp.

<400> SEQUENCE: 9

Ala Glu Cys Ser Ile Arg Gly Leu Tyr Pro Thr Lys Ser Ile Ser Thr
 1               5                  10                  15

Trp Lys Lys Trp Ser Pro Ser Glu Ser
            20                  25

<210> SEQ ID NO 10
<211> LENGTH: 63
<212> TYPE: PRT
<213> ORGANISM: Drosophila sp.

<400> SEQUENCE: 10

Asp Gln Leu Trp Arg Leu Leu Thr Ser Leu Cys Met His Ala Gly Ile
 1               5                  10                  15

Leu His Leu Ala Ile Thr Leu Ile Phe Gln His Leu Phe Leu Ala Asp
            20                  25                  30

Leu Glu Arg Leu Ile Gly Thr Val Arg Thr Ala Ile Val Tyr Ile Met
        35                  40                  45

Ser Gly Phe Ala Gly Asn Leu Thr Ser Ala Ile Leu Val Pro His
    50                  55                  60

<210> SEQ ID NO 11
<211> LENGTH: 175
<212> TYPE: PRT
<213> ORGANISM: Drosophila sp.

<400> SEQUENCE: 11

Gly Leu Leu Ala Gly Val Ile Cys Gly Cys Leu Leu Thr Met Ser Leu
 1               5                  10                  15

Val Pro Phe Thr Thr Phe Ser Lys Tyr Gly Arg Lys Lys Lys Ile Asn
            20                  25                  30

Leu Ile Trp Thr Cys Val Leu Phe His Val Val Tyr Thr Ala Met
        35                  40                  45

Ile Val Thr Phe Tyr Ile His Pro Ser Glu Phe His Ser Ile Ser Phe
    50                  55                  60

Val Asp Met Phe Ser Asn Ser Asn Gly Tyr Asp Asn Phe Thr Asn Ala
 65                  70                  75                  80

Asp His His Gly Val Asp Val Ser Ser Asn Thr Arg Tyr Ser Gln
                85                  90                  95

Thr Gln Asn Ser Gln Tyr Tyr Tyr His His His Ser Asp Asp Ile Ile
                100                 105                 110

Arg Lys Ser Val Thr Phe Thr Glu Lys Ala Leu Val Ser His Ile Leu
            115                 120                 125

Tyr Pro Thr Ala Pro Arg Lys Thr Ser Ala Gln Gln Trp Gln Glu Val
        130                 135                 140

Glu Tyr Ser Arg Ser Phe Asn His Leu Ser Asn Tyr Ser Asp Arg Ile
145                 150                 155                 160

Lys Lys Ser Ile Gly Asn Ile Ser Lys Leu Lys Gln Val Phe Thr
                165                 170                 175

<210> SEQ ID NO 12
<211> LENGTH: 343
<212> TYPE: PRT
<213> ORGANISM: Homo sapiens
```

<400> SEQUENCE: 12

```
Leu Val His Ser His Glu Leu Pro Leu Asp Pro Ala Lys Leu Asp Met
  1               5                  10                  15

Leu Val Ala Leu Ala Gln Ser Asn Glu Gln Gly Gln Val Cys Tyr Gln
             20                  25                  30

Glu Leu Val Asp Leu Ile Ser Ser Lys Arg Ser Ser Phe Lys Arg
         35                  40                  45

Ala Ile Ala Asn Gly Gln Arg Ala Leu Pro Arg Asp Gly Pro Leu Asp
     50                  55                  60

Glu Pro Gly Leu Gly Val Tyr Lys Arg Phe Val Arg Tyr Val Ala Tyr
 65                  70                  75                  80

Glu Ile Leu Pro Cys Glu Val Asp Arg Arg Trp Tyr Phe Tyr Arg His
             85                  90                  95

Arg Ser Cys Pro Pro Val Phe Met Ala Ser Val Thr Leu Ala Gln
                100                 105                 110

Ile Ile Val Phe Leu Cys Tyr Gly Ala Arg Leu Asn Lys Trp Val Leu
            115                 120                 125

Gln Thr Tyr His Pro Glu Tyr Met Lys Ser Pro Leu Val Tyr His Pro
        130                 135                 140

Gly His Arg Ala Arg Ala Trp Arg Phe Leu Thr Tyr Met Phe Met His
145                 150                 155                 160

Val Gly Leu Glu Gln Leu Gly Phe Asn Ala Leu Leu Gln Leu Met Ile
                165                 170                 175

Gly Val Pro Leu Glu Met Val His Gly Leu Leu Arg Ile Ser Leu Leu
            180                 185                 190

Tyr Leu Ala Gly Val Leu Ala Gly Ser Leu Thr Val Ser Ile Thr Asp
        195                 200                 205

Met Arg Ala Pro Val Val Gly Gly Ser Gly Gly Val Tyr Ala Leu Cys
    210                 215                 220

Ser Ala His Leu Ala Asn Val Val Met Asn Trp Ala Gly Met Arg Cys
225                 230                 235                 240

Pro Tyr Lys Leu Leu Arg Met Val Leu Ala Leu Val Cys Met Ser Ser
                245                 250                 255

Glu Val Gly Arg Ala Val Trp Leu Arg Phe Ser Pro Pro Leu Pro Ala
            260                 265                 270

Ser Gly Pro Gln Pro Ser Phe Met Ala His Leu Ala Gly Ala Val Val
        275                 280                 285

Gly Val Ser Met Gly Leu Thr Ile Leu Arg Ser Tyr Glu Glu Arg Leu
    290                 295                 300

Arg Asp Gln Cys Gly Trp Trp Val Val Leu Leu Ala Tyr Gly Thr Phe
305                 310                 315                 320

Leu Leu Phe Ala Val Phe Trp Asn Val Phe Ala Tyr Asp Leu Leu Gly
                325                 330                 335

Ala His Ile Pro Pro Pro
            340
```

<210> SEQ ID NO 13
<211> LENGTH: 348
<212> TYPE: PRT
<213> ORGANISM: Caenorhabditis elegans

<400> SEQUENCE: 13

```
Arg Lys Thr Tyr Arg His Gln Phe Asn Gln Leu Arg Thr Gly Asp Glu
  1               5                  10                  15

Thr Glu Ile Pro Met Ser Thr Leu Ala Ser Arg Ile Glu Thr Arg Lys
             20                  25                  30

Ile Pro Leu Thr Asn Gly Gln Ile His Ala Ile Lys Glu Ala Pro Asp
         35                  40                  45

Glu Leu Val Asp Ile Asp Gly Phe Gln Lys Ile Val Thr Ser Lys Ala
     50                  55                  60

Ala Gln Arg Ser Thr Ile Lys Arg Ile Met Tyr Asp Met Ala Asp Pro
 65                  70                  75                  80

Ile Met Ser Asp Ser Gln Lys Ile Glu Val His Ser Tyr Ile Asp Ser
                 85                  90                  95

Tyr Ser Trp Cys Pro Pro Ile Phe Met Leu Leu Ile Thr Ile Ile
            100                 105                 110

Gln Val Gly Ile Phe Phe Tyr Trp Glu Ser Asp Gly Gly Arg Ser
        115                 120                 125

Ile Trp Thr Asp Cys Ala Gly Cys Phe Val His His Asn His Thr Ala
    130                 135                 140

Pro Gly Ile Phe Ile Phe Ala Pro Lys Leu Arg Gly Glu Ala Trp Arg
145                 150                 155                 160

Phe Thr Ser Tyr Met Phe Leu His Ala Gly Leu Asn His Leu Leu Gly
                165                 170                 175

Asn Val Ile Ile Gln Leu Leu Val Gly Ile Pro Leu Glu Val Ala His
            180                 185                 190

Lys Ile Trp Arg Ile Gly Pro Ile Tyr Leu Leu Ala Val Thr Ser Gly
        195                 200                 205

Ser Leu Leu Gln Tyr Ala Ile Asp Pro Asn Ser Leu Leu Val Gly Ala
    210                 215                 220

Ser Ala Gly Val Tyr Ala Leu Ile Phe Ala His Val Ala Asn Val Ile
225                 230                 235                 240

Leu Asn Trp His Glu Met Pro Leu Arg Trp Ile Arg Val Leu Val Leu
                245                 250                 255

Phe Val Phe Ile Phe Leu Asp Phe Gly Gly Ala Ile His Arg Arg Phe
            260                 265                 270

Tyr Thr Asn Asp Cys Asp Ser Val Ser His Leu Ala His Ile Ala Gly
        275                 280                 285

Ala Val Thr Gly Leu Phe Gly Tyr Val Val Leu Tyr Asn Val Val
    290                 295                 300

Glu His Arg Ile Glu Lys Ile Ile Arg Tyr Val Cys Leu Phe Leu Tyr
305                 310                 315                 320

Ser Ala Phe Phe Ala Thr Thr Ile Ile Phe Val Ile Val Arg Gln Pro
                325                 330                 335

Tyr Ser Lys Asn Leu Trp Asn Asn Glu Asn Cys Ser
            340                 345
```

<210> SEQ ID NO 14
<211> LENGTH: 20
<212> TYPE: PRT
<213> ORGANISM: Drosophila sp.

```
<400> SEQUENCE: 14

Pro Val Pro Ile Pro Ser Asp Ser Val Leu Leu Ala Gln Ser Arg Tyr
  1               5                  10                  15

Cys Leu His Lys
             20

<210> SEQ ID NO 15
<211> LENGTH: 27
<212> TYPE: PRT
<213> ORGANISM: Drosophila sp.

<400> SEQUENCE: 15

Arg Glu Thr Arg Gln Pro Thr Lys Asp Cys Gly Thr Ser Gln Gly Thr
  1               5                  10                  15

Ile His Gln Ile Phe Phe His Asn Phe Leu Val
             20                  25

<210> SEQ ID NO 16
<211> LENGTH: 20
<212> TYPE: PRT
<213> ORGANISM: Drosophila sp.

<400> SEQUENCE: 16

Gly Arg Asn Tyr Phe Tyr Gln Arg Leu Asn Ala Ser Glu Leu Phe Glu
  1               5                  10                  15

Leu Phe Asp Lys
             20

<210> SEQ ID NO 17
<211> LENGTH: 17
<212> TYPE: PRT
<213> ORGANISM: Drosophila sp.

<400> SEQUENCE: 17

Gly Arg Asn Tyr Phe Tyr Gln Arg Leu Asn Thr Ser Gly Pro Val Ala
  1               5                  10                  15

Ile

<210> SEQ ID NO 18
<211> LENGTH: 21
<212> TYPE: PRT
<213> ORGANISM: Drosophila sp.
<220> FEATURE:
<221> NAME/KEY: MOD_RES
<222> LOCATION: (8)
<223> OTHER INFORMATION: Lys or Arg

<400> SEQUENCE: 18

Glu Glu Lys Arg Thr Val His Xaa Asp Leu Ala Ala Arg Asn Val Thr
  1               5                  10                  15

Val Arg Thr Thr Ala
             20

<210> SEQ ID NO 19
<211> LENGTH: 193
<212> TYPE: PRT
<213> ORGANISM: Drosophila sp.
```

<400> SEQUENCE: 19

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu

<210> SEQ ID NO 20
<211> LENGTH: 193
<212> TYPE: PRT
<213> ORGANISM: Drosophila sp.

<400> SEQUENCE: 20

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Ile Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Gln Asp Glu His Thr Arg
        115                 120                 125

Arg Glu Leu Ala Lys Met Lys Gln Glu Pro Val Arg Ser Glu Glu Gly
    130                 135                 140

Arg Asp Met Ala Asn Arg Ile Ser Ala Phe Gly Tyr Leu Glu Cys Ser
145                 150                 155                 160

```
Ala Lys Thr Lys Glu Gly Val Arg Glu Val Phe Glu Met Ala Thr Arg
            165                 170                 175

Ala Gly Leu Gln Val Arg Lys Asn Lys Arg Arg Gly Cys Pro Ile
            180                 185                 190

Leu

<210> SEQ ID NO 21
<211> LENGTH: 192
<212> TYPE: PRT
<213> ORGANISM: Drosophila sp.

<400> SEQUENCE: 21

Met Thr Thr Ile Arg Lys Lys Leu Val Ile Val Gly Asp Gly Ala Cys
  1               5                  10                  15

Gly Lys Thr Cys Leu Leu Ile Val Phe Ser Lys Asp Gln Phe Pro Glu
                 20                  25                  30

Val Tyr Val Pro Thr Val Phe Glu Asn Tyr Val Ala Asp Ile Glu Val
             35                  40                  45

Asp Gly Lys Gln Val Glu Leu Ala Leu Trp Asp Thr Ala Gly Gln Glu
         50                  55                  60

Asp Tyr Asp Arg Leu Arg Pro Leu Ser Tyr Pro Asp Thr Asp Val Ile
 65                  70                  75                  80

Leu Met Cys Phe Ser Val Asp Ser Pro Asp Ser Leu Glu Asn Ile Pro
                 85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Pro Asn Thr Ile
            115                 120                 125

Arg Asp Leu Ala Lys Met Lys Gln Glu Pro Val Lys Pro Gln Glu Gly
130                 135                 140

Arg Ala Met Ala Glu Lys Ile Asn Ala Phe Ala Tyr Leu Glu Cys Ser
145                 150                 155                 160

Ala Lys Ser Lys Glu Gly Val Arg Asp Val Phe Glu Thr Ala Thr Arg
            165                 170                 175

Ala Ala Leu Gln Val Lys Lys Arg Lys Thr Arg Cys Leu Leu Leu
            180                 185                 190

<210> SEQ ID NO 22
<211> LENGTH: 196
<212> TYPE: PRT
<213> ORGANISM: Drosophila sp.

<400> SEQUENCE: 22

Met Ala Ala Ile Arg Lys Lys Leu Val Val Val Gly Asp Gly Ala Cys
  1               5                  10                  15

Gly Lys Thr Cys Leu Leu Ile Val Phe Ser Lys Asp Glu Phe Pro Glu
                 20                  25                  30

Val Tyr Val Pro Thr Val Phe Glu Asn Tyr Val Ala Asp Ile Glu Val
             35                  40                  45

Asp Gly Lys Gln Val Glu Leu Ala Leu Trp Asp Thr Ala Gly Gln Glu
         50                  55                  60

Asp Tyr Asp Arg Leu Arg Pro Leu Ser Tyr Pro Asp Thr Asp Val Ile
 65                  70                  75                  80

Leu Met Cys Phe Ser Val Asp Ser Pro Asp Ser Leu Glu Asn Ile Pro
                 85                  90                  95
```

```
Glu Lys Trp Val Pro Glu Val Lys His Phe Cys Pro Asn Val Pro Ile
            100                 105                 110

Ile Leu Val Ala Asn Lys Lys Asp Leu Arg Ser Asp Glu His Val Arg
        115                 120                 125

Thr Glu Leu Ala Arg Met Lys Gln Glu Pro Val Arg Thr Asp Asp Gly
    130                 135                 140

Arg Ala Met Ala Val Arg Ile Gln Ala Tyr Asp Tyr Leu Glu Cys Ser
145                 150                 155                 160

Ala Lys Thr Lys Glu Gly Val Arg Glu Val Phe Glu Thr Ala Thr Arg
                165                 170                 175

Ala Ala Leu Gln Lys Arg Tyr Gly Ser Gln Asn Gly Cys Ile Asn Cys
            180                 185                 190

Cys Lys Val Leu
        195

<210> SEQ ID NO 23
<211> LENGTH: 192
<212> TYPE: PRT
<213> ORGANISM: Drosophila sp.

<400> SEQUENCE: 23

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Ala
        35                  40                  45

Lys Pro Ile Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Asn Pro Ala Ser Phe Glu Asn Val Arg Ala Lys
                85                  90                  95

Trp Tyr Pro Glu Val Arg His His Cys Pro Ser Thr Pro Ile Ile Leu
            100                 105                 110

Val Gly Thr Lys Leu Asp Leu Arg Asp Asp Lys Asn Thr Ile Glu Lys
        115                 120                 125

Leu Arg Asp Lys Lys Leu Ala Pro Ile Thr Tyr Pro Gln Gly Leu Ala
    130                 135                 140

Met Ala Lys Glu Ile Gly Ala Val Lys Tyr Leu Glu Cys Ser Ala Leu
145                 150                 155                 160

Thr Gln Lys Gly Leu Lys Thr Val Phe Asp Glu Ala Ile Arg Ser Val
                165                 170                 175

Leu Cys Pro Val Leu Gln Pro Lys Ser Lys Arg Lys Cys Ala Leu Leu
            180                 185                 190

<210> SEQ ID NO 24
<211> LENGTH: 192
<212> TYPE: PRT
<213> ORGANISM: Drosophila sp.

<400> SEQUENCE: 24

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30
```

```
Ile Pro Thr Val Phe Asp Asn Tyr Ser Ala Asn Val Met Val Asp Ala
        35                  40                  45

Lys Pro Ile Asn Leu Gly Leu Trp Asp Thr Ala Gly Gln Glu Asp Tyr
 50                  55                  60

Asp Arg Leu Arg Pro Leu Ser Tyr Pro Gln Thr Asp Val Phe Leu Ile
 65                  70                  75                  80

Cys Phe Ser Leu Val Asn Pro Ala Ser Phe Glu Asn Val Arg Ala Lys
                85                  90                  95

Trp Phe Pro Glu Val Arg His His Cys Pro Ser Val Pro Ile Ile Leu
            100                 105                 110

Val Gly Thr Lys Leu Asp Leu Arg Asp Asp Lys Gln Thr Ile Glu Lys
            115                 120                 125

Leu Lys Asp Lys Leu Thr Pro Ile Thr Tyr Pro Gln Gly Leu Ala
130                 135                 140

Met Ala Lys Glu Ile Ala Ala Val Lys Tyr Leu Glu Cys Ser Ala Leu
145                 150                 155                 160

Thr Gln Lys Gly Leu Lys Thr Val Phe Asp Glu Ala Ile Arg Ser Val
                165                 170                 175

Leu Cys Pro Val Val Arg Gly Pro Lys Arg His Lys Cys Ala Leu Leu
            180                 185                 190

<210> SEQ ID NO 25
<211> LENGTH: 192
<212> TYPE: PRT
<213> ORGANISM: Drosophila sp.

<400> SEQUENCE: 25

Met Gln Ala Ile Lys Cys Val Val Val Gly Asp Gly Ala Val Gly Lys
 1               5                  10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Ser
        35                  40                  45

Lys Pro Val Asn Leu Gly Leu Trp Asp Thr Ala Gly Gln Glu Asp Tyr
 50                  55                  60

Asp Arg Leu Arg Pro Leu Ser Tyr Pro Gln Thr Asp Val Phe Leu Ile
 65                  70                  75                  80

Cys Phe Ser Leu Val Ser Pro Ala Ser Tyr Glu Asn Val Arg Ala Lys
                85                  90                  95

Trp Phe Pro Glu Val Arg His His Cys Pro Ser Thr Pro Ile Ile Leu
            100                 105                 110

Val Gly Thr Lys Leu Asp Leu Arg Asp Asp Lys Asp Thr Ile Glu Lys
            115                 120                 125

Leu Lys Glu Lys Lys Leu Ala Pro Ile Thr Tyr Pro Gln Gly Leu Ala
130                 135                 140

Leu Ala Lys Glu Ile Asp Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Gln Pro Thr Arg Gln Gln Lys Arg Ala Cys Ser Leu Leu
            180                 185                 190

<210> SEQ ID NO 26
<211> LENGTH: 192
<212> TYPE: PRT
<213> ORGANISM: Drosophila sp.
```

```
<400> SEQUENCE: 26

Met Gln Ala Ile Lys Cys Val Val Gly Asp Gly Ala Val Gly Lys
 1               5                  10                  15

Thr Cys Leu Leu Ile Ser Tyr Thr Thr Asn Ala Phe Pro Gly Glu Tyr
             20                  25                  30

Ile Pro Thr Val Phe Asp Asn Tyr Ser Ala Asn Val Met Val Asp Gly
             35                  40                  45

Lys Pro Val Asn Leu Gly Leu Trp Asp Thr Ala Gly Gln Glu Asp Tyr
         50                  55                  60

Asp Arg Leu Arg Pro Leu Ser Tyr Pro Gln Thr Asp Val Phe Leu Ile
 65                  70                  75                  80

Cys Phe Ser Leu Val Ser Pro Ala Ser Phe Glu Asn Val Arg Ala Lys
                 85                  90                  95

Trp Tyr Pro Glu Val Arg His His Cys Pro His Thr Pro Ile Leu Leu
                100                 105                 110

Val Gly Thr Lys Leu Asp Leu Arg Asp Lys Asp Thr Ile Glu Arg
            115                 120                 125

Leu Arg Asp Lys Lys Leu Ala Pro Ile Thr Tyr Pro Gln Gly Leu Ala
        130                 135                 140

Met Ala Arg Glu Ile Gly Ser Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Val Lys Lys Pro Gly Lys Lys Cys Thr Val Phe
            180                 185                 190

<210> SEQ ID NO 27
<211> LENGTH: 191
<212> TYPE: PRT
<213> ORGANISM: Drosophila sp.

<400> SEQUENCE: 27

Met Gln Thr Ile Lys Cys Val Val Gly Asp Gly Ala Val Gly Lys
 1               5                  10                  15

Thr Cys Leu Leu Ile Ser Tyr Thr Thr Asn Lys Phe Pro Ser Glu Tyr
             20                  25                  30

Val Pro Thr Val Phe Asp Asn Tyr Ala Val Thr Val Met Ile Gly Gly
             35                  40                  45

Glu Pro Tyr Thr Leu Gly Leu Phe Asp Thr Ala Gly Gln Glu Asp Tyr
         50                  55                  60

Asp Arg Leu Arg Pro Leu Ser Tyr Pro Gln Thr Asp Val Phe Leu Val
 65                  70                  75                  80

Cys Phe Ser Val Val Ser Pro Ser Ser Phe Glu Asn Val Lys Glu Lys
                 85                  90                  95

Trp Val Pro Glu Ile Thr His His Cys Gln Lys Thr Pro Phe Leu Leu
                100                 105                 110

Val Gly Thr Gln Ile Asp Leu Arg Asp Glu Asn Ser Thr Leu Glu Lys
            115                 120                 125

Leu Ala Lys Asn Lys Gln Lys Pro Ile Thr Met Glu Gln Gly Glu Lys
        130                 135                 140

Leu Ala Lys Glu Leu Lys Ala Val Lys Tyr Val Glu Cys Ser Ala Leu
145                 150                 155                 160
```

```
                                        -continued

Thr Gln Lys Gly Leu Lys Asn Val Phe Asp Glu Ala Ile Leu Ala Ala
                165                 170                 175

Leu Glu Pro Pro Glu Pro Thr Lys Lys Arg Lys Cys Lys Phe Leu
            180                 185                 190
```